(12) United States Patent
Karla et al.

(10) Patent No.: US 12,324,653 B2
(45) Date of Patent: Jun. 10, 2025

(54) CONNECTOR FOR MEDICAL EQUIPMENT

(71) Applicant: Welch Allyn, Inc., Skaneateles Falls, NY (US)

(72) Inventors: Sean R. Karla, Syracuse, NY (US); Thaddeus J. Wawro, Auburn, NY (US); Raymond A. Lia, Auburn, NY (US); Scott A. Martin, Camillus, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 0 days.

(21) Appl. No.: 18/375,131

(22) Filed: Sep. 29, 2023

(65) Prior Publication Data
US 2024/0023819 A1 Jan. 25, 2024

Related U.S. Application Data

(62) Division of application No. 16/107,514, filed on Aug. 21, 2018, now Pat. No. 11,793,412.
(Continued)

(51) Int. Cl.
*F16L 39/00* (2006.01)
*A61B 5/021* (2006.01)
(Continued)

(52) U.S. Cl.
CPC .......... *A61B 5/02141* (2013.01); *A61B 5/022* (2013.01); *F16L 37/084* (2013.01); *F16L 37/0841* (2013.01); *F16L 37/56* (2013.01); *A61B 2560/0406* (2013.01); *A61B 2560/0443* (2013.01); *A61B 2562/225* (2013.01)

(58) Field of Classification Search
CPC ......... F16L 47/00; F16L 47/06; F16L 47/065; F16L 47/08; F16L 2201/44; F16L 2201/40; F16L 39/02; F16L 39/06; F16L 39/00; F16L 39/04; F16L 33/006; F16L 33/00; F16L 21/00; F16L 21/002; F16L 21/02;
(Continued)

(56) References Cited

U.S. PATENT DOCUMENTS 4,186,946 A * 2/1980 Snow ...................... F16L 37/53
29/523
4,753,268 A 6/1988 Palau
(Continued)

*Primary Examiner* — Aaron M Dunwoody
(74) *Attorney, Agent, or Firm* — Lee & Hayes, P.C.

(57) ABSTRACT

A male bayonet connector includes a first shaft having a first distal end portion having a first sealing surface configured to form a substantially fluid-tight seal with a female connector, a first proximal end portion opposite the first distal end portion, a first lumen extending substantially along a first longitudinal axis of the first shaft from the first distal end portion to the first proximal end portion, and a first channel formed on an outer surface of the first shaft between the first sealing surface and the first proximal end portion. The first channel at least partially extends circumferentially around the first longitudinal axis. The first channel is also defined by a first distal wall, a first proximal wall opposite the first distal wall, and a first central region extending from the first distal wall to the first proximal wall. The first distal wall includes a first axial length that is at least one of curved or at an acute angle relative to the first longitudinal axis.

20 Claims, 15 Drawing Sheets

Related U.S. Application Data

(60) Provisional application No. 62/548,672, filed on Aug. 22, 2017.

(51) Int. Cl.
    *A61B 5/022*     (2006.01)
    *F16L 37/084*     (2006.01)
    *F16L 37/56*     (2006.01)

(58) Field of Classification Search
    CPC ....... F16L 21/035; F16L 21/022; F16L 37/56; F16L 37/0841
    See application file for complete search history.

(56) References Cited

U.S. PATENT DOCUMENTS

| | | | |
|---|---|---|---|
| 5,232,020 A * | 8/1993 | Mason | A61F 7/02 |
| | | | 137/454.2 |
| 5,636,887 A | 6/1997 | Petropoulos et al. | |
| 2005/0057042 A1 | 3/2005 | Wicks | |
| 2011/0204622 A1 * | 8/2011 | Lewis | F16L 37/0841 |
| | | | 285/313 |
| 2016/0258561 A1 | 9/2016 | Hiroi | |
| 2019/0059754 A1 | 2/2019 | Karla et al. | |

* cited by examiner

CONNECTOR FOR MEDICAL EQUIPMENT

CROSS-REFERENCE TO RELATED APPLICATIONS

This application is a divisional of U.S. application Ser. No. 16/107,514, filed Aug. 21, 2018, which claims the benefit of U.S. Provisional Application No. 62/548,672, filed Aug. 22, 2017, the entire disclosures of which are incorporated herein by reference.

TECHNICAL FIELD

This application is directed to medical equipment, and in particular, to connectors for use with medical equipment configured to determine hemodynamic parameters associated with a patient.

BACKGROUND

Some non-invasive patient monitoring devices are configured to inflate a cuff to a pressure above a patient's systolic blood pressure in order to occlude arterial blood flow in the limb on which the cuff is disposed. Once above systole, the cuff can be deflated, and the systolic and diastolic pressures of the patient can be calculated based on measurements made during cuff deflation.

In situations in which the patient's blood pressure and/or other hemodynamic parameters may be monitored over extended periods, it may be desirable to leave the cuff disposed about the patient's limb even when the cuff is not being used to obtain measurements. In such examples, it is common for the patient to be transferred between several different locations of the healthcare facility to receive care, and different cuff inflation devices or other patient monitoring system components may be connected to the cuff at each of the different locations in order to obtain hemodynamic parameter measurements at such locations. Accordingly, there is a need for reliable and universally compatible means for temporarily fluidly connecting the cuff with different patient monitoring systems disposed at various locations throughout the healthcare facility.

The various example embodiments of the present disclosure are directed toward overcoming one or more of the deficiencies associated with known cuff connection devices.

SUMMARY

In an example embodiment of the present disclosure, a male bayonet connector includes a first shaft having a first distal end portion with a first sealing surface configured to form a substantially fluid-tight seal with a female connector, a first proximal end portion opposite the first distal end portion, a first lumen extending substantially along a first longitudinal axis of the first shaft from the first distal end portion to the first proximal end portion, and a first channel formed on an outer surface of the first shaft between the first sealing surface and the first proximal end portion. The first channel at least partially extends circumferentially around the first longitudinal axis. The first channel is also defined by a first distal wall, a first proximal wall opposite the first distal wall, and a first central region extending from the first distal wall to the first proximal wall. The first distal wall includes a first axial length that is at least one of curved or at an acute angle relative to the first longitudinal axis.

In another example embodiment of the present disclosure, a male bayonet connector includes a first shaft having a first distal end portion including a first sealing surface configured to form a substantially fluid-tight seal with a female connector, a first proximal end portion opposite the first distal end portion, a first lumen extending substantially along a first longitudinal axis of the first shaft from the first distal end portion to the first proximal end portion, and a first channel formed on an outer surface of the first shaft. The first channel includes a distal end adjacent to the first sealing surface. The first sealing surface includes a first axial length that is at least one of curved or at an acute angle relative to the first longitudinal axis.

In a further example embodiment of the present disclosure, a male bayonet connector includes a first shaft having a first distal end portion including a first sealing surface configured to form a substantially fluid-tight seal with a female connector, a first proximal end portion opposite the first distal end portion, a first lumen extending substantially along a first longitudinal axis of the first shaft from the first distal end portion to the first proximal end portion, and a first channel disposed between the first sealing surface and the first proximal end portion. The first channel extends at least partially circumferentially around the first longitudinal axis. The first channel is also at least partly defined by a first central region and a first proximal wall. At least part of the first proximal wall extends radially from the first central region to an outer surface of the first shaft. The male bayonet connector also includes a first axial groove oriented substantially parallel to the first longitudinal axis, the first axial groove extending proximally from the first proximal wall.

In another example embodiment, a male bayonet connector includes a first shaft having a first distal end portion including a first sealing surface configured to form a substantially fluid-tight seal with a female connector, a first proximal end portion opposite the first distal end portion, a first lumen extending substantially along a first longitudinal axis of the first shaft from the first distal end portion to the first proximal end portion, and a first channel formed on an outer surface of the first shaft between the first sealing surface and the first proximal end portion, the first channel at least partially extending circumferentially around the first longitudinal axis. The bayonet connector also includes a second shaft having a second distal end portion including a second sealing surface configured to form an additional substantially fluid-tight seal with the female connector, a second proximal end portion opposite the second distal end portion, a second lumen extending substantially along a second longitudinal axis of the second shaft from the second distal end portion to the second proximal end portion, and a second channel formed on an outer surface of the second shaft between the second sealing surface and the second proximal end portion, the second channel at least partially extending circumferentially around the second longitudinal axis. The bayonet connector also includes a connector detachably connecting the first shaft with the second shaft.

DETAILED DESCRIPTION

Figure 1:
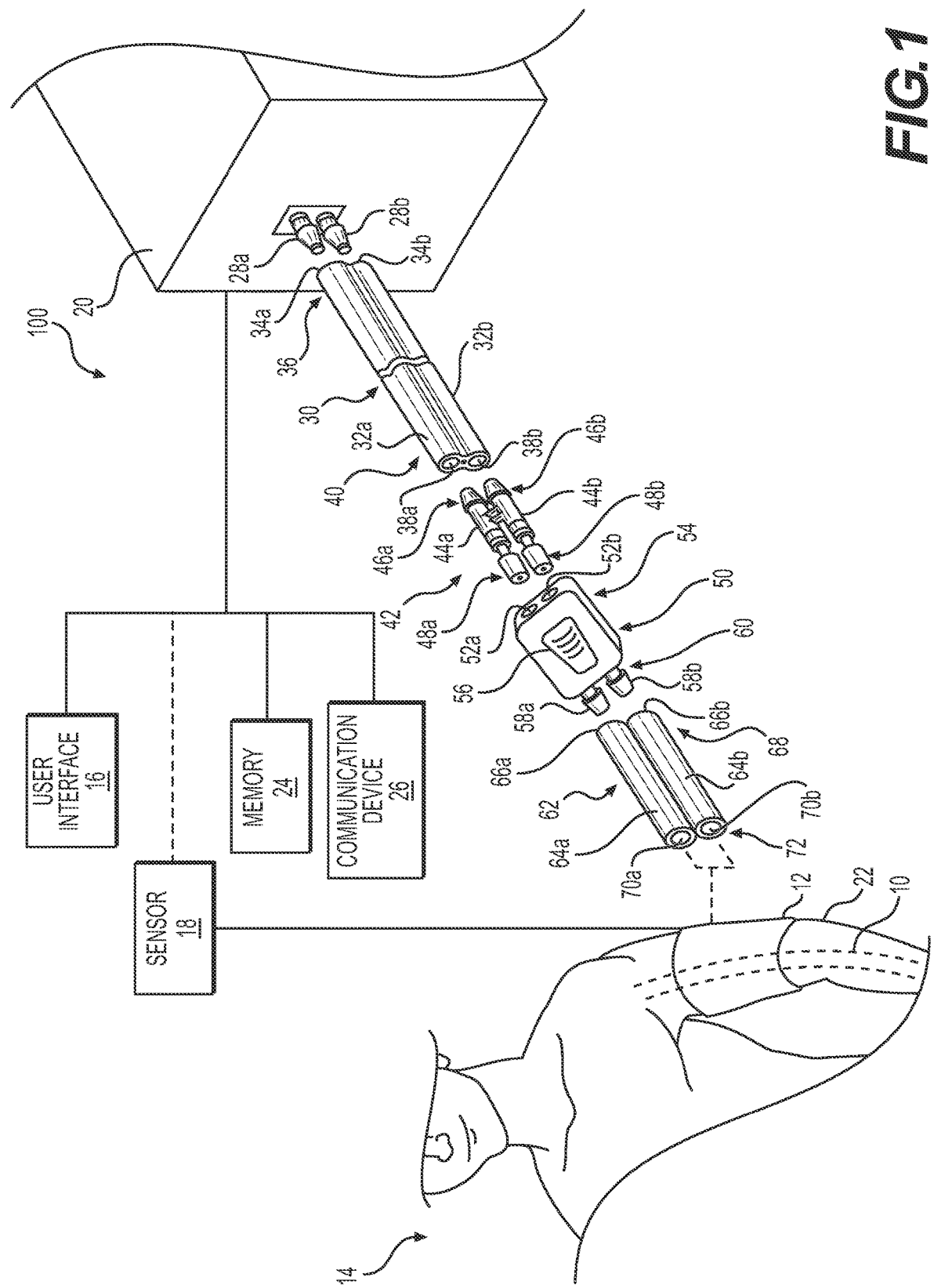
FIG. 1 includes a partial schematic illustration of a patient monitoring system according to an example embodiment of the present disclosure.

FIG. 1 illustrates a patient monitoring system 100, according to an example embodiment of the present disclosure. The system 100 can be configured to monitor a patient, and in some embodiments, to determine a hemodynamic parameter of the patient. As used herein, the term "hemodynamic parameter" can include an indication of cardiac or vascular health, such as, for example, an indication of cardiac, circulatory, or vascular functionality. Specifically, a hemodynamic parameter can include a heart rate, a blood pressure, a vessel compliance, a saturation of hemoglobin with oxygen in arterial blood (i.e., an $SpO_2$ measurement), an aortic index, an augmentation index, reflected wave ratio, or an indication of treatment. Blood pressure can include systolic, suprasystolic, diastolic, or mean atrial pressure. It is understood that such blood pressures may be represented as a systolic blood pressure over a diastolic blood pressure, and that a mean or average blood pressure may be represented as an average systolic blood pressure over an average diastolic blood pressure. Moreover, an indication of treatment can include a parameter reflecting the affect of a drug treatment, or one or more treatments of a disease state.

The system 100 can include a cuff 12 configured to at least to partially occlude the movement of blood through a blood vessel 10 of a patient 14 such as an artery, vein, or the like. In some embodiments, the cuff 12 can be configured to completely occlude an artery of patient 14. In any of the embodiments described herein, however, the system 100 may be tuned and/or otherwise configured to determine one or more hemodynamic parameters of the patient 14, such as a blood pressure of the patient 14, without completely occluding the blood vessel 10. In such embodiments, the system 100, and/or components thereof, may determine the blood pressure of the patient 14 before the cuff 12 is inflated to a pressure associated with complete occlusion of the blood vessel 10 and/or before a systolic blood pressure of the patient 14 is reached. Although shown in FIG. 1 surrounding an arm 22 of the patient 14, the cuff 12 may be adapted for placement on (i.e., around) any suitable body part of patient 14, including, for example, a wrist, a finger, an upper thigh, an ankle, or any other like limb or body part. In addition, one or more cuffs 12 could be placed at different locations about the patient 14 for use with the system 100.

The cuff 12 can include one or more bladders or other like inflatable devices, and the pressure or volume within the cuff 12 may be controlled by any known inflation device (not shown). Such inflation devices can include a pump or similar device configured to controllably inflate and/or deflate the inflatable device of the cuff 12. For example, such inflation devices could supply the cuff 12 with a fluid to increase the pressure or volume of the cuff 12. In other embodiments, one or more inflation devices could include mechanical, electrical, or chemical devices configured to occlusion of the blood vessel 10 via the cuff 12. Such inflation devices may comprise a component of the system 100 and may be included within and/or operably connected to, for example, a controller 20 of the system 100. In some embodiments, such inflation devices can inflate the cuff 12 to or towards a target inflation pressure, and may be configured to generally maintain the cuff 12 at any desired inflation pressure for a desired period of time. In some embodiments, the target inflation pressure may be less than or equal to the systolic pressure of the patient 14. Alternatively, in further embodiments the target pressure may be greater than the systolic pressure of the patient 14. In example embodiments, the system 100 may determine the blood pressure of the patient 14 without inflating the cuff to the systolic pressure. Accordingly, even in embodiments in which algorithms, controllers, and/or other components of the system 100 employ a target inflation pressure that is equal to or greater than the systolic pressure, the system 100 may discontinue inflation of the cuff 12 at an inflation pressure less than such a target inflation pressure. Although such embodiments may use a target inflation pressure equal to or greater than the systolic pressure, discontinuing inflation of the cuff 100 at a pressure below such a target inflation pressure may avoid patient discomfort during blood pressure determination.

The system 100 can further include a sensor 18 configured to receive a signal associated with the patient 14. In some embodiments, the sensor 18 can be configured to receive a signal associated with an at least partially occluded vessel 10 of the patient 14. Such an input signal can arise from blood movement through the partially occluded vessel 10 or from a signal associated with an occluded blood vessel 10. The sensor 18 could sample multiple times at various intervals. In yet other embodiments, the sensor 18 could provide an indication of blood vessel movement, such as, for example, oscillations arising from vascular expansion or contraction. For example, the sensor 18 could be configured to detect a pressure or volume of cuff 12 that may vary periodically with the cyclic expansion and contraction of the blood vessel of the patient 14. In particular, the sensor 18 could determine a blood pressure, various pulses of blood through the blood vessel 10, an oxygen saturation of the blood, or any other hemodynamic parameter associated with the patient 14 using an auscultation, oscillometric, or other known measurement method.

In some embodiments, the sensor 18 could detect a volume or a pressure associated with cuff 12. For example, the sensor 18 could include a pressure transducer or other like pressure sensor, and may be located within, on, or about the cuff 12 or other parts of the system 100. In such embodiments, the sensor 18 may be configured to sense, measure, detect, monitor, calculate, and/or otherwise "determine" one or more blood pressure pulses associated with the patient 14. Each blood pressure "pulse" may be indicative of, for example, the movement of blood through the blood vessel 10 by the heart of the patient 14 during systole, and the number of such pulses per minute may comprise the heart rate of the patient 14.

The controller 20 may comprise and/or otherwise include one or more processors, microprocessors, programmable logic controllers, and/or other like components configured to control one or more operations of the cuff 12, the cuff inflation devices, the sensor 18, and/or other components of the system 100 connected to the controller 20. For example, the controller 20 can control inflation and/or deflation of the cuff 12 via control of the inflation devices described above.

In some embodiments, the controller 20 can sense, measure, detect, monitor, calculate, and/or otherwise determine a blood pressure of the patient 14 based on one or more of the hemodynamic parameters determined by the sensor 18. This determination may be based on one or more output signals received from sensor 18, as described above. The controller 20 may also control inflation of cuff 12 (via one or more of the inflation devices described herein) toward a target inflation pressure, or generally maintaining inflation of cuff 12 at about the target pressure. Such a target inflation pressure may be a pressure that is greater than, equal to, or less than, for example, a systolic pressure of the patient 14 and/or the mean arterial pressure of the patient. For example, as noted above, the system 100 may determine the blood pressure of the patient 14 without inflating the cuff to the systolic pressure. Accordingly, even in embodiments in which the controller 20 employs a target inflation pressure that is equal to or greater than the systolic pressure for purposes of cuff inflation, algorithms of the controller 20 may discontinue inflation of the cuff 12 at an inflation pressure less than such a target inflation pressure. Despite the use of such example target inflation pressures, the controller 20 may determine the blood pressure of the patient 14 without completely occluding the blood vessel 10.

Although not shown in FIG. 1, in additional example embodiments, the system 100 can optionally include a signal analysis module. For example, the signal analysis module may be configured to analyze one or more signals received from the sensor 18 using one or more processors of the controller 20. For example, the signal analysis module can include one or more filters configured to filter a signal associated with the sensor 18 or the controller 20. Such filters can include band-pass, high-pass, or low-pass filters.

As illustrated in FIG. 1, the system 100 may also include a memory 24 operably connected to the controller 20. The memory 24 may include, for example, a hard drive, a thumb drive, and/or any other like fixed or removable storage device known in the art. Such memory 24 may comprise random access memory, read-only memory, transient memory, non-transient memory, and/or any other like information storage means. In such embodiments, the memory 24 may be configured to store signals, data, values, curves, thresholds, and/or any other like information received from the sensor 18. The memory 24 may also be configured to store signals, data, values, thresholds, curves, and/or any other like information determined by the controller 20 during the various operations described herein. For example, the memory 24 may be configured to store one or more pressure pulses, pulse profiles, pulse heights, pulse curves, target inflation pressures, pressure thresholds, and/or other like information. Additionally, the memory 24 may be configured to store one or more algorithms, protocols and/or other like programs associated with calculating and/or otherwise determining the blood pressure of the patient 14. Additionally, the memory 24 may be configured to store one or more sets of values corresponding to points on one or more pulse curves. Such information may be recalled and/or otherwise utilized by the controller 20 during one or more blood pressure determination methods described herein.

The system 100 can further include a user interface 16 configured to provide communication to the patient 14 or one or more operators. For example, the user interface 16 could include a display configured to communicate and/or otherwise output one or more hemodynamic parameters. The user interface 16 may further include one or more speakers or other like audio devices configured to communicate and/or otherwise output information to the patient 14 and/or a user operator of the system 100. In further embodiments, the system 100 may include one or more transmitters, network devices, routers, Bluetooth® devices, WiFi® devices, radio devices, and/or other like communication device 26 configured to transmit data to a remote location and/or to a remote device. In such embodiments, the communication device 26 may enable the transmission of information to or from the controller 20. It is understood, that such communication devices 26 may facilitate the transmission of such information via wired or wireless means. For example, in any of the embodiments described herein, one or more components of the system 100, such as the controller 20, may be disposed remote from a remainder of the components of the system 100. In such embodiments, for example, the controller 20 may be disposed in a different location of a healthcare facility than the cuff 12, user interface 16, or other components of the system 100. Alternatively, in further embodiments, the controller 20 may be in a first healthcare facility and a remainder of the components of the system 100 may be located in a second healthcare facility different from the first facility. In such embodiments, the various components of the system 100 may be in communication and/or otherwise operably connected via the communication devices 26 described herein.

In addition to the components outlined above, the system 100 may include various other components as required, such as, for example, a power source and/or a user input device. One or more components described herein may be combined or may be separate independent components of the system. Moreover, the various components of the system 100 could be integrated into a single processing unit or may operate as separate processors. In operation, one or more processors can be configured to operate in conjunction with one or more software programs to provide the functionality of the system 100. For example, one or more of the components described above with respect to the system 100 may include one or more hardware components and/or one or more software components configured to control operation of such components and/or of the system 100.

The system 100 of the present disclosure may also include one or more components configured to fluidly connect the cuff 12 with the controller 20, and in particular, with one or more inflation devices operably connected to the controller 20. For example, the controller 20 may include first and second connectors 28a, 28b fluidly coupled to one or more of the inflation devices described herein. The first and second connectors 28a, 28b may comprise male barbs or other like connectors defining a respective lumen through which pressurized air or other fluids may pass from the inflation devices to tubing 30 fluidly connected to the one or more connectors 28a, 28b. For example, the tubing 30 may comprise dual-lumen tubing having first and second connected conduit sections 32a, 32b sharing a substantially smooth integrated outer surface. In such embodiments, an orifice 34a of the first section 32a at a proximal end 36 of the tubing 30 may be configured to form a substantially fluid-tight connection with the first connector 28a. Similarly, an orifice 34b of the second section 32b at the proximal end 36 of the tubing 30 may be configured to form a substantially fluid-tight connection with the second connector 28b. Alternatively, in other embodiments, the tubing 30 may comprise single-lumen tubing, and a first section of the single-lumen tubing may be configured to form a substantially fluid-tight connection with the first connector 28a while a second section of the single-lumen tubing 30 may be configured to form a substantially fluid-tight connection with the second connector 28b. For ease of discussion, the tubing 30 shall be described herein as dual-lumen tubing unless otherwise noted. In any of the embodiments described herein, the tubing 30 may comprise a flexible, durable, medically approved material such as a thermoplastic elastomer, and the tubing 30 may be made from processes including extrusion molding.

The first section 32a of the tubing 30 may also include an orifice 38a at a distal end 40 of the tubing 30, and the second section 32b may include a similar orifice 38b at the distal end 40. The orifices 38a, 38b may be configured to form a substantially fluid-tight connection with a male bayonet connector 42 of the present disclosure. As will be described in greater detail below, the bayonet connector 42 may have various different configurations, and any of the bayonet connectors described herein may be employed by the system 100 in order to assist in fluidly connecting the cuff 12 with the controller 20 and/or other components of the system 100. In some examples, the bayonet connector 42 may comprise a dual-shaft connector, while in other examples, the bayonet connector 42 may comprise a single-shaft connector. For ease of discussion, the bayonet connector 42 shall be described herein as dual-shaft connector unless otherwise noted.

The bayonet connector 42 may include, for example, first and second shafts 44a, 44b, and a proximal end portion 46a of the first shaft 44a may be configured to form a substantially fluid-tight connection with the first section 32a of the tubing 30, while a proximal end portion 46b of the second shaft 44b may be configured to form a substantially fluid-tight connection with the second section 32b of the tubing 30. In particular, a barb or other like connector may be formed at each of the proximal end portions 46a, 46b, and such barbs may be inserted into the respective orifices 38a, 38b of the tubing 30 to form such a substantially fluid-tight connection between the bayonet connector 42 and the tubing 30. In some examples, the barbs formed at each of the proximal end portions 46a, 46b may be substantially similar to and/or the same as the first and second connectors 28a, 28b described above. The first and second shafts 44a, 44b of the bayonet connector 42 may also include respective distal end portions 48a, 48b, and the distal end portion 48a of the first shaft 44a may be disposed opposite the proximal end portion 46a while the distal end portion 48b of the second shaft 44b may be disposed opposite the proximal end portion 46b. The first and second shafts 44a, 44b may define respective lumens passing therethrough from the respective proximal end portions 46a, 46b to the respective distal end portions 48a, 48b. Additionally, as will be described in greater detail below, the distal end portion 48a of the first shaft 44a may include a sealing surface configured to form a substantially fluid-tight seal with a female connector 50, and the distal end portion 48b of the second shaft 44b may also include a sealing surface configured to form a substantially fluid-tight seal with the female connector 50.

An example female connector 50 of the present disclosure may be configured to assist in coupling the male bayonet connector 42 to the cuff 12. The female connector 50 may have any number of orifices configured to mate with one or more portions of the bayonet connector 42 in order to form a substantially fluid-tight connection therewith. For example, the female connector 50 may include first and second orifices 52a, 52b at a proximal end portion 54 thereof. The first orifice 52a may be configured to mate with the first shaft 44a, and the second orifice 52b may be configured to mate with the second shaft 44b. In particular, the first orifice 52a may be sized to accept passage of at least part of the distal end portion 48a therethrough such that a sealing surface of the distal end portion 48a may form a substantially fluid-tight seal with a corresponding component of the female connector 50. Likewise, the second orifice 52b may be sized to accept passage of at least part of the distal end portion 48b therethrough such that a sealing surface of the distal end portion 48b may form a substantially fluid-tight seal with a corresponding component of the female connector The female connector 50 may also include one or more actuators 56 configured to assist coupling the bayonet connector 42 with the female connector 50 and/or decoupling the bayonet connector 42 from the female connector 50.

It is understood that the female connector 50 may be configured to transmit fluid delivered from the bayonet connector 42 distally to the cuff 12. Accordingly, the female connector 50 may also include first and second connectors 58a, 58b disposed at a distal end portion 60 thereof. In some examples, the first and second connectors 58a, 58b may be substantially similar to and/or the same as the first and second connectors 28a, 28b described above. For instance, the first and second connectors 58a, 58b may be configured to form a substantially fluid-tight connection with respective sections of an additional piece of tubing 62 that is fluidly connected to the cuff 12. For example the tubing 62 may be substantially similar to and/or the same as the tubing 30 described above. In such examples, the tubing 62 may include a first section 64a, and a second section 64b connected to the first section 64a. In such examples, the first connector 58a of the female connector 50 may be configured to form a substantially fluid-tight connection with the first section 64a of the tubing 62, and the second connector 58b may be configured to form a substantially fluid-tight connection with the second section 64b of the tubing 62. In particular, the first connector 58a may be inserted into an orifice 66a at a proximal end 68 of the tubing 62 to form such a substantially fluid-tight connection between the female connector 50 and the tubing 62. Likewise, the second connector 58b may be inserted into an orifice 66b at the proximal end 68 of the tubing 62 to form an additional substantially fluid-tight connection between the female connector 50 and the tubing 62. The first section 64a may also form an orifice 70a at a distal end 72 of the tubing 62, and the second section 64b may also form an orifice 70b at the distal end 72. It is understood that, as with the tubing 30, the first section 64a may form a lumen and/or other fluid passage extending from the orifice 66a to the orifice 70a, and the second section 64b may form an additional lumen or other fluid passage extending from the orifice 66b to the orifice 70b. As shown schematically in FIG. 1, the distal end 72 of the tubing 62 may be fluidly connected to the cuff 12 and, in some examples, one or more adapters, connectors, or additional components of the system 100 may be employed to form such a fluid connection.

Figure 2:
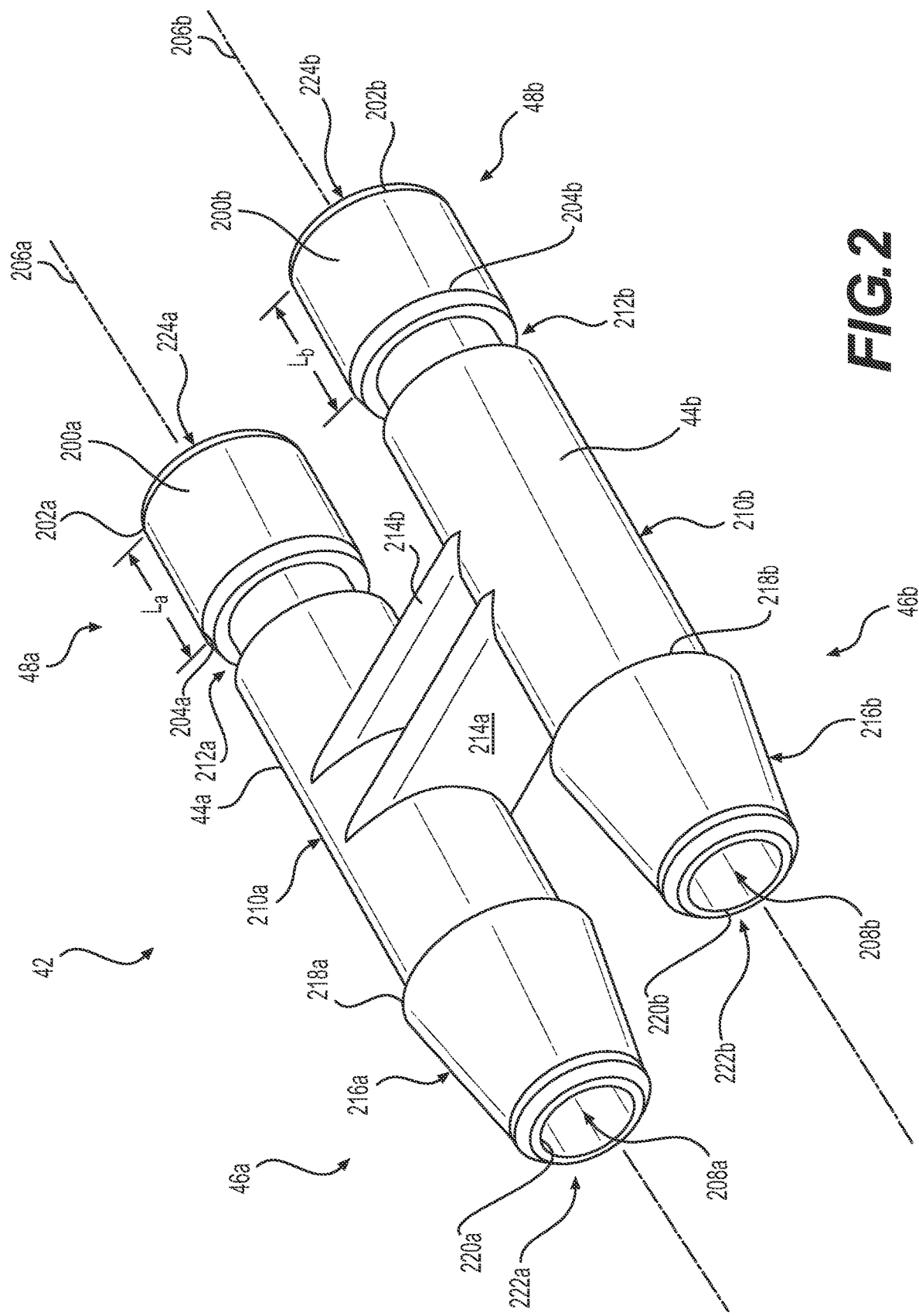
FIG. 2 is an isometric view of an example male bayonet connector of the present disclosure.

FIG. 2 illustrates the example bayonet connector 42 of FIG. 1 in greater detail. As shown in FIG. 2, the distal end portion 48a of the first shaft 44a may include a first sealing surface 200a, and the distal end portion 48b of the second shaft 44b may include a second sealing surface 200b. In the example embodiment of FIG. 2, the sealing surfaces 200a, 200b may be substantially annular and may have a substantially constant diameter. In additional example embodiments, however, at least one of the sealing surfaces 200a, 200b may have any other configuration including configurations in which a diameter thereof is not constant along an axial length of the respective sealing surface 200a, 200b. Such examples will be described in greater detail below. In any of the examples described herein, the sealing surfaces 200a, 200b may be configured to form a substantially fluid-tight seal with the female connector 50 described above.

In some examples, the sealing surface 200a may include, for example, an axial length La extending from a distal end 202a of the sealing surface 200a to a proximal end 204a of the sealing surface 200a opposite the distal end 202a. Likewise, the sealing surface 200b may include an axial length Lb extending from a distal end 202b of the sealing surface 200b to a proximal end 204b of the sealing surface 200b opposite the distal end 202b. The first shaft 44a may define a first longitudinal axis 206a extending substantially centrally therethrough from the distal end portion 48a to the proximal end portion 46a, and the second shaft 44b may define a second longitudinal axis 206b extending substantially centrally therethrough from the distal end portion 48b to the proximal end portion 46b. Additionally, as can be seen in FIG. 2, the first shaft 44a may include a first lumen 208a extending substantially along the longitudinal axis 206a from the distal end portion 48a to the proximal end portion 46a. Likewise, the second shaft 44b may include a second lumen 208b extending substantially along the longitudinal axis 206b from the distal end portion 48b to the proximal end portion 46b. In any of the examples described herein, the longitudinal axis 206a may be substantially parallel to the longitudinal axis 206b.

Outer surfaces 210a, 210b of the first and second shafts 44a, 44b may extend substantially circumferentially around the respective longitudinal axes 206a, 206b, and the first and second shafts 44a, 44b may be substantially cylindrical in shape. Alternatively, the first and second shafts 44a, 44b may have any other shape useful in mating with, for example, the female connector 50 and the tubing 30. For example, the first shaft 44a may include a first channel 212a of any shape, size, and/or other configuration formed on the outer surface 210a of the first shaft 44a, and the second shaft 44b may include a second channel 212b, having a configuration that is substantially similar to and/or the same as the first channel 212a, formed on the outer surface 210b. In any of the embodiments described herein, the first and second channels 212a, 212b may be formed on the respective outer surfaces 210a, 210b between the respective sealing surfaces 200a, 200b and the respective proximal end portions 46a, 46b of the shafts 44a, 44b. As shown in FIG. 2, the first channel 212a may, at least partially, extend circumferentially around the longitudinal axis 206a, and the second channel 212b may, at least partially, extend circumferentially around the longitudinal axis 206b. Additionally, as will be described in greater detail below, the first and second channels 212a, 212b may be defined, at least in part, by distal and/or proximal sidewalls extending substantially radially away from the respective longitudinal axes 206a, 206b. Such sidewalls may have any shape, size, angle, contour, profile, and/or other configuration useful in releasably connecting the bayonet connector 42 with the female connector 50.

In some examples, the bayonet connector 42 may include one or more links 214a, 214b extending substantially radially from the respective outer surfaces 210a, 210b, and the one or more links 214a, 214b may connect the first shaft 44a with the second shaft 44b. In such examples, the bayonet connector 42 may comprise a dual shaft connector, and the links 214a, 214b may, for example, space the first shaft 44a from the second shaft 44b to facilitate connecting the dual lumen tubing 30 to the first and second proximal end portions 46a, 46b. For example, the first shaft 44a may include a first connector 216a disposed at the proximal end portion 46a, and the second shaft 44b may include a second connector 216b disposed at the proximal end portion 46b. The connectors 216a, 216b may include respective distal ends 218a, 218b and proximal ends 220a, 220b, and the connectors 216a, 216b may also include axial lengths tapered toward the respective longitudinal axes 206a, 206b from the distal ends 218a, 218b to the proximal ends 220a, 220b. The proximal ends 220a, 220b of the connectors 216a, 216b may form proximal ends 222a, 222b of the respective shafts 44a, 44b. In some examples, the connectors 216a, 216b may be substantially similar to and/or the same as the first and second connectors 28a, 28b described above. For instance, the connectors 216a, 216b may be configured to form a substantially fluid-tight connection with the respective sections 32a, 32b of the tubing 30. In particular, the first connector 216a may be inserted into the orifice 38a at the distal end 40 of the tubing 30 to form such a substantially fluid-tight connection between the bayonet connector 42 and the tubing 30. Likewise, the second connector 216b may be inserted into the orifice 38b at the distal end 40 of the tubing 30 to form a substantially fluid-tight connection between the bayonet connector 42 and the tubing 30.

Figure 3:
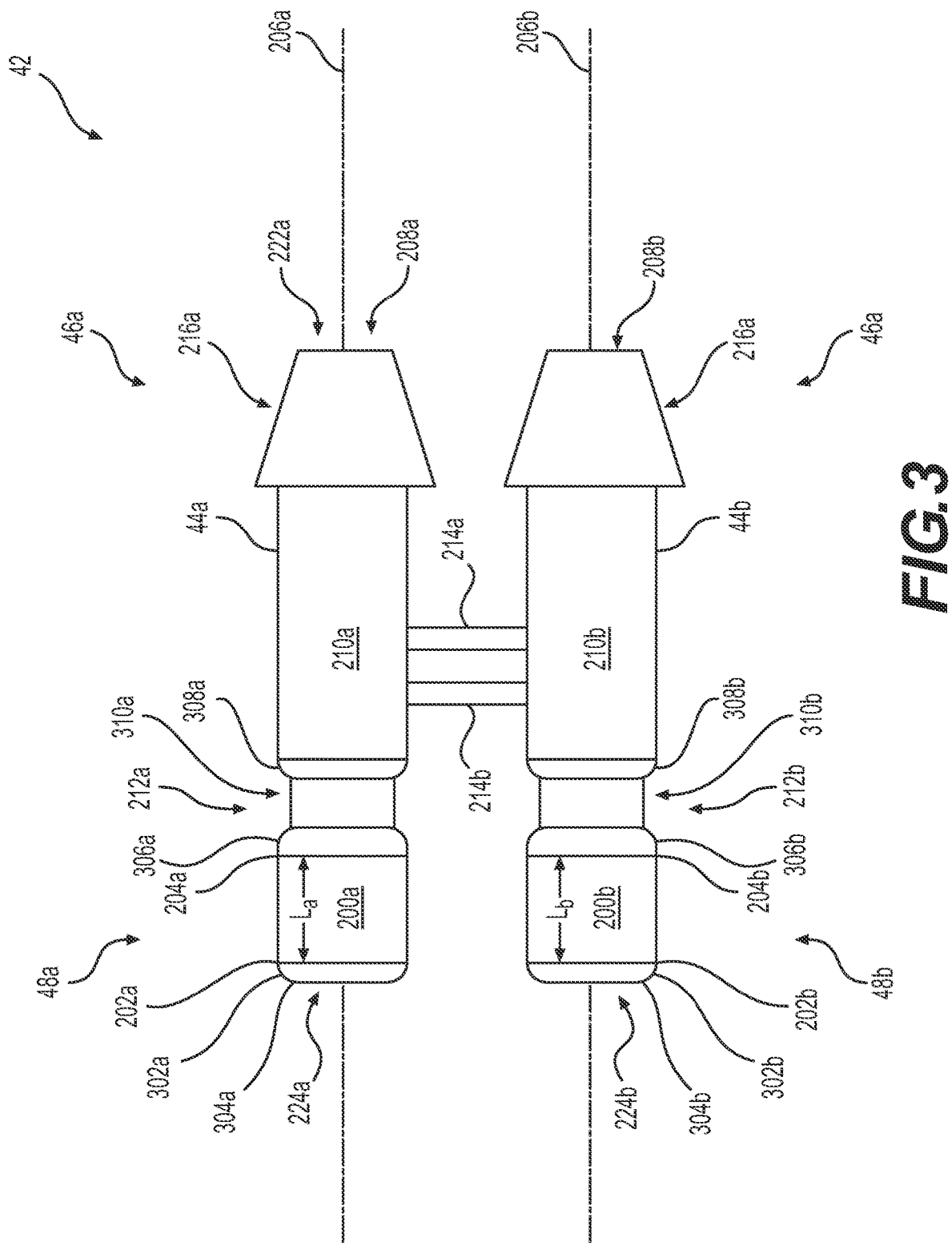
FIG. 3 is a top view of the example male bayonet connector shown in FIG. 2.

FIG. 3 illustrates another view of the bayonet connector 42 shown in FIG. 2. As shown in FIG. 3, the bayonet connector 42 may include various walls and/or other components that define at least part of the channels 212a, 212b and/or the distal end portions 48a, 48b. For example, the distal end portions 48a, 48b of the first and second shafts 44a, 44b may include respective walls 302a, 302b that are chamfered, curved, tapered, rounded, and/or otherwise angled from the distal ends 202a, 202b of the respective sealing surfaces 200a, 200b to respective distal ends 304a, 304b of the walls 302a, 302b. In such examples, the curvature of the respective walls 302a, 302b may make it easier to insert the distal end portions 48a, 48b into the female connector 50 and to remove the distal end portions 48a, 48b from the female connector 50.

Additionally, the first channel 212a of the bayonet connector 42 may be defined, at least in part, by a distal wall 306a, a proximal wall 308a opposite the distal wall 306a, and a central region 310a extending from the distal wall 306a to the proximal wall 308a. Likewise, the second channel 212b may be defined, at least in part, by a distal wall 306b, a proximal wall 308b opposite the distal wall 306b, and a central region 310b extending from the distal wall 306b to the proximal wall 308b. As can be seen in the example embodiment of FIG. 3, the distal walls 306a, 306b may each extend substantially circumferentially about the respective longitudinal axes 206a, 206b of the shafts 44a, 44b. Additionally, the distal wall 306a may include a profile and/or axial length that is at least one of curved, concave, convex, tapered, rounded, and/or angled relative to the longitudinal axis 206a, and the distal wall 306b may include a similar profile and/or axial length that is at least one of curved and/or angled relative to the longitudinal axis 206b.

Figure 4:
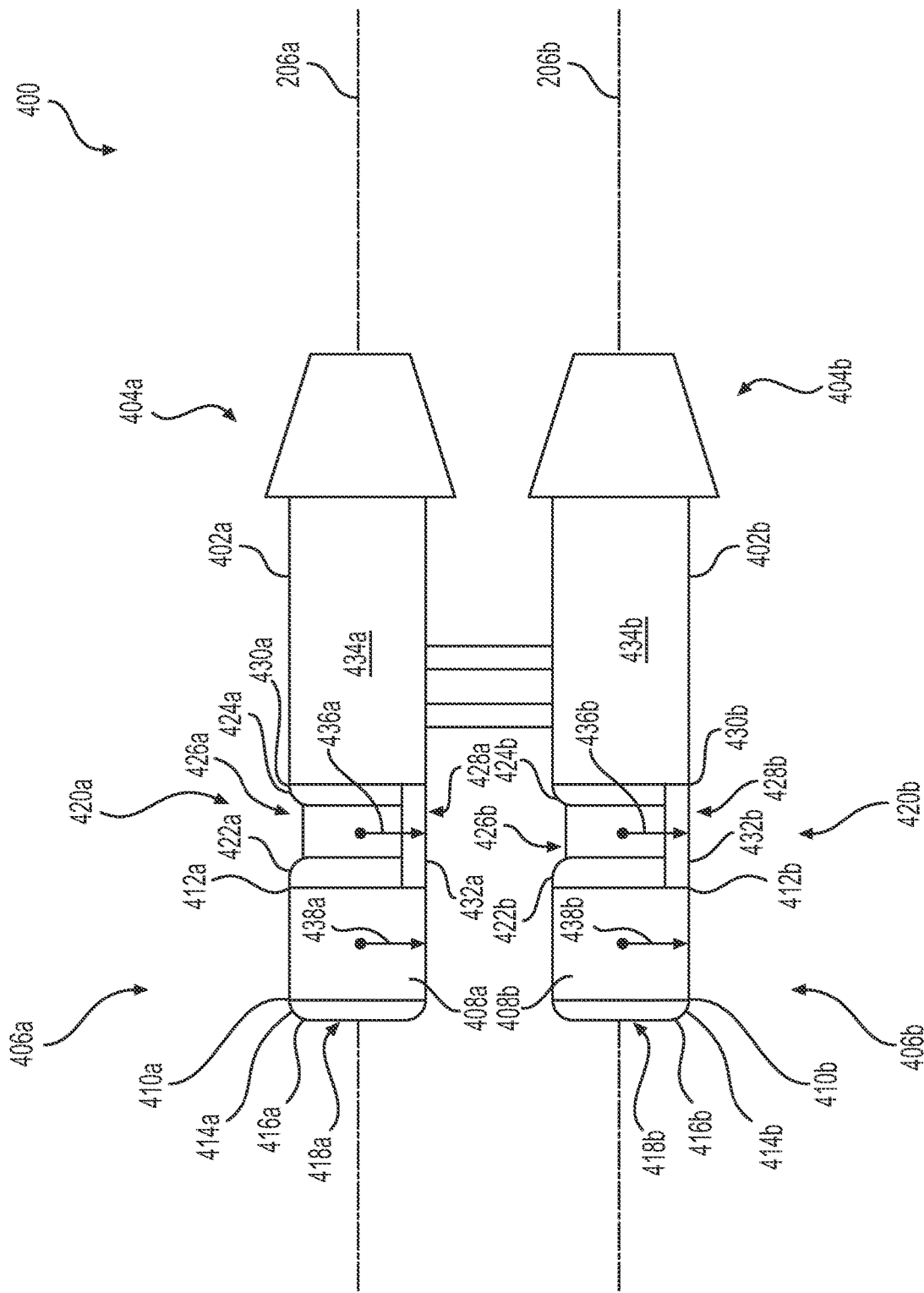
FIG. 4 is a top view of another example male bayonet connector of the present disclosure.
Figure 5:
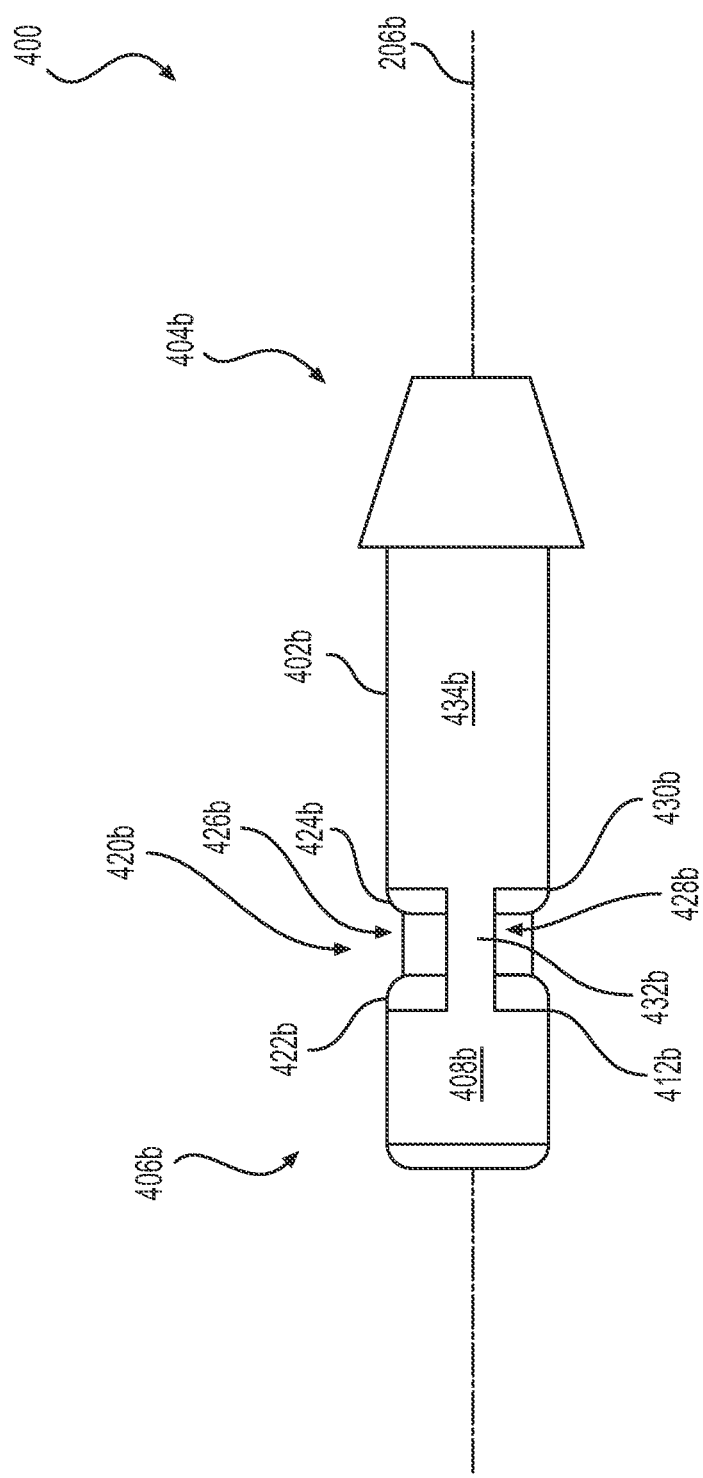
FIG. 5 is a side view of the example male bayonet connector shown in FIG. 4.

FIGS. 4 and 5 illustrate another example bayonet connector 400 of the present disclosure. In example embodiments, any of the structures, functions, and/or other aspects of the bayonet connector 42 described herein with respect to FIGS. 1-3 may be included in the bayonet connector 400 and/or in any of the other example bayonet connectors described herein. Further, one or more of the structures, functions, and/or features of the bayonet connector 400 described with respect to FIGS. 4 and 5 may be incorporated into any of the bayonet connectors of the present disclosure. For example, the bayonet connector 400 may include first and second shafts 402a, 402b having respective longitudinal axes 206a, 206b extending substantially centrally therethrough. The first shaft 402a may include a first proximal end portion 404a, a first distal end portion 406a opposite the first proximal end portion 406a, and a first sealing surface 408a at the distal end portion 406a having a distal end 410a and a proximal end 412a opposite the distal end 412a. Likewise, the second shaft 402b may include a second proximal end portion 404b, a second distal end portion 406b opposite the second proximal end portion 406b, and a second sealing surface 408b at the distal end portion 406b having a distal end 410b and a proximal end 412b opposite the distal end 412b. As described above with respect to the bayonet connector 42, the distal end portions 406a, 406b of the first and second shafts 402a, 402b may include respective walls 414a, 414b that are chamfered, curved, tapered, rounded, and/or otherwise angled from the distal ends 410a, 410b of the respective sealing surfaces 408a, 408b to respective distal ends 416a, 416b of the walls 414a, 414b. In such examples, the curvature of the respective walls 414a, 414b may make it easier to insert the distal end portions 406a, 406b into the female connector 50 and to remove the distal end portions 406a, 406b from the female connector 50. The distal ends 416a, 416b of the walls 414a, 414b may, in some examples, form at least part of respective distal ends 418a, 418b of the first and second shafts 402a, 402b.

The first shaft 402a of the bayonet connector 400 may also include a first channel 420a of any shape, size, and/or other configuration formed on an outer surface 434a of the first shaft 402a, and the second shaft 402b may include a second channel 420b, having a configuration that is substantially similar to and/or the same as the first channel 420a, formed on an outer surface 434b thereof. The first and second channels 420a, 420b may be formed on the respective outer surfaces 434a, 434b between the respective sealing surfaces 408a, 408b and the respective proximal end portions 404a, 404b of the shafts 402a, 402b. As shown in FIG. 4, the first channel 420a may at least partially extend circumferentially around the longitudinal axis 206a, and the second channel 420b may at least partially extend circumferentially around the longitudinal axis 206b.

The distal walls 422a, 422b may each extend substantially circumferentially about the respective longitudinal axes 206a, 206b of the shafts 402a, 402b. Additionally, the distal wall 422a may include a profile and/or axial length that is at least one of curved, concave, convex, tapered, rounded, and/or angled relative to the longitudinal axis 206a, and the distal wall 402b may include a similar profile and/or axial length that is at least one of curved and/or angled relative to the longitudinal axis 206b. Further, in any of the examples described herein, the proximal wall 424a of the channel 420a may also have a profile and/or axial length that is at least one of curved, concave, convex, tapered, rounded, and/or angled relative to the longitudinal axis 206a, and the proximal wall 424b of the channel 420b may include a configuration that is substantially similar to and/or the same as the proximal wall 424a.

The first channel 420a may also include a first rib 428a extending radially outwardly from the central region 426a, and the first rib 428a may extend from the proximal wall 424a of the channel 420a to the distal wall 422a. Likewise, the second channel 420b may include a second rib 428b extending radially outwardly from the central region 426b, and the second rib 428b may extend from the proximal wall 424b of the channel 420b to the distal wall 422b. Such ribs 428a, 428b may extend radially at any location within the respective channels 420a, 420b and about the respective longitudinal axes 206a, 206b and, in some examples, at least one of the channels 420a, 420b may include more than one rib. Such ribs 428a, 428b may assist in aligning the bayonet connector 400 with the female connector 50 as the bayonet connector 400 is inserted at least partly into the female connector 50. Further, each of the ribs 428a, 428b may have any desired dimensions, shape, and/or other configuration so as to assist with such alignment. For example, the proximal walls 424a, 424b of the channels 420a, 420b may extend proximally from the central region 426a, 426b to respective proximal ends 430a, 430b thereof. In such examples, one or more of the ribs 428a, 428b may include a radially outermost rib surface 432a, 432b that mates with such proximal ends 430a, 430b. The radially outermost rib surfaces 432a, 432b may be disposed at respective radial distances 436a, 436b away from the longitudinal axes 206a, 206b of the respective shafts 402a, 404b. In such examples, at least the respective proximal ends 430a, 430b of the proximal walls 424a, 424b may be disposed at respective radial distances away from the longitudinal axes 206a, 206b of the respective shafts 402a, 404b that are substantially equal to the respective radial distances 436a, 436b. In addition, at least the sealing surfaces 408a, 408b may be disposed at respective radial distances 438a, 438b away from the longitudinal axes 206a, 206b of the respective shafts 402a, 404b. In such embodiments, the radial distances 436a, 436b associated with the radially outermost surfaces 432a, 432b may be substantially equal to the corresponding radial distances 438a, 438b associated with the sealing surfaces 408a, 408b. Further, in such embodiments, one or more of the radially outermost rib surfaces 432a, 432b may extend substantially parallel to the longitudinal axes 206a, 206b of the respective shafts 402a, 404b. Alternatively, one or more of the radially outermost rib surfaces 432a, 432b may be curved, tapered, convex, concave, and/or have any other configuration.

FIG. 5 is a side view of the bayonet connector 400 described above with respect to FIG. 4. As can be seen in FIG. 5, a radially outermost rib surface 432b of at least one of the ribs 428b may comprise an axial length that extends, from the proximal end 412b to the proximal end 430b, substantially parallel to the longitudinal axis 206b. Further, in some examples, the outer surface 434b, the radially outermost rib surface 432b, and the sealing surface 408b may comprise a single substantially rounded outer surface of the shaft 402b.

FIGS. 6-13 illustrate partial side views of additional example bayonet connectors of the present disclosure. One or more of the structures, functions, and/or features of the bayonet connectors described with respect to FIGS. 6-13 may be incorporated into any of the bayonet connectors of the present disclosure. Additionally, although each of FIGS. 6-13 illustrate only a single shaft, it is understood that the structures, functions, and/or features of the bayonet connectors described with respect to FIGS. 6-13 may be incorporated into both shafts of an example dual-shaft bayonet connector.

Figure 6:
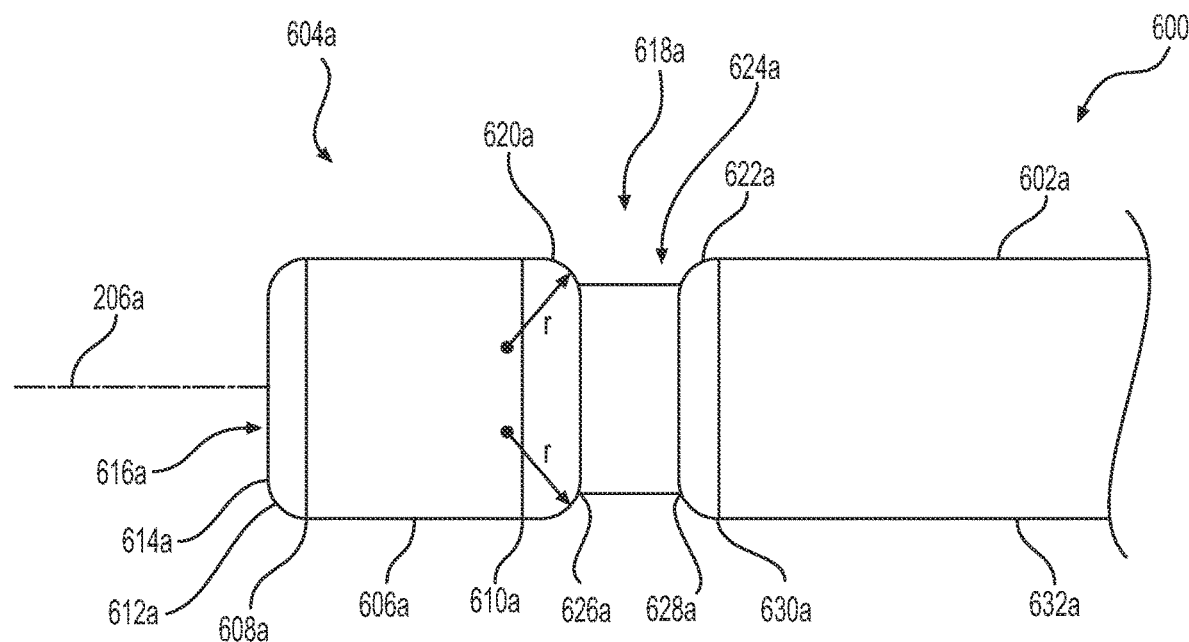
FIG. 6 is a side view of a portion of an example male bayonet connector according to a further embodiment of the present disclosure.

FIG. 6 illustrates a portion of an example bayonet connector 600 and, in particular, a portion of an example shaft 602a thereof. Such an example shaft 602a may include a distal end portion 604a having a sealing surface 606a configured to form a substantially fluid-tight seal with the female connector 50. The sealing surface 606a may have a distal end 608a and a proximal end 610a opposite the distal end 608a. As described above with respect to the bayonet connector 42, the distal end portion 604a may include a wall 612a that is chamfered, curved, tapered, rounded, and/or otherwise angled from the distal end 608a of the sealing surface 606a to a distal end 614a of the wall 612a. In such examples, the curvature of the wall 612a may make it easier to insert the distal end portion 604a into the female connector 50 and to remove the distal end portion 604a from the female connector 50. The distal end 614a of the wall 612a may, in some examples, form at least part of a distal end 616a of the shaft 602a.

The shaft 602a of the bayonet connector 600 may also include a channel 618a of any shape, size, and/or other configuration formed on an outer surface 632a of the shaft 602a. The channel 618a may be formed on the outer surface 632a between the sealing surface 606a and the proximal end portion of the shaft 602a (not shown). Further, the channel 618a may at least partially extend circumferentially around the longitudinal axis 206a. As shown in FIG. 6, the channel 618a may be defined by and/or may otherwise include a distal wall 620a, a proximal wall 622a opposite the distal wall 620a, and a central region 624a extending from the distal wall 620a to the proximal wall 622a. The distal wall 620a may be substantially similar in shape, size, and/or configuration to at least one of the distal walls 306a, 422a described above. For example, the distal wall 620a may comprise a substantially curved, substantially rounded, substantially chamfered, and/or substantially convex sidewall of the channel 618a. In particular, the distal sidewall 620a may include an axial length (as illustrated by at least part of the side profile of the distal sidewall 620a shown in FIG. 6) that extends proximally from the proximal end 610a of the sealing surface 606a to a distal end 626a of the central region 624a. The proximal wall 622a may comprise a substantially curved, substantially rounded, substantially chamfered, substantially concave, and/or substantially convex sidewall of the channel 618a that includes an axial length extending proximally from a proximal end 628a of the central region 624a to a proximal end 630a. In some examples, the proximal wall 622a of the channel 618a may have a configuration that is substantially similar to and/or the same as the distal wall 620a. Additionally, the distal wall 620a may have a radius r having any desired value. For example, the radius r may be between approximately 0.1 inch and approximately 10 inches. In further examples, the radius r may be between approximately 0.5 inches and approximately 5 inches. In still further examples, the radius r may have a value greater than or less than the values noted above.

Figure 7:
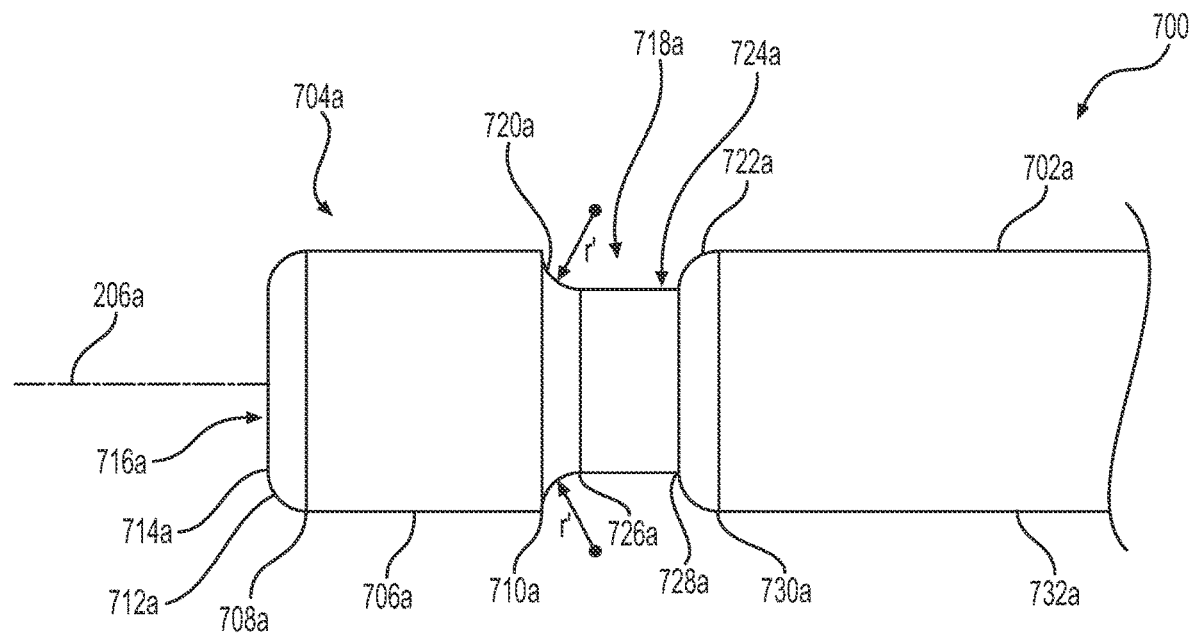
FIG. 7 is a side view of a portion of an example male bayonet connector according to another embodiment of the present disclosure.

FIG. 7 illustrates a portion of another example bayonet connector 700 and, in particular, a portion of an example shaft 702a thereof. Such an example shaft 702a may include a distal end portion 704a having a sealing surface 706a configured to form a substantially fluid-tight seal with the female connector 50. The sealing surface 706a may have a distal end 708a and a proximal end 710a opposite the distal end 708a. As described above with respect to the bayonet connector 42, the distal end portion 704a may include a wall 712a that is chamfered, curved, tapered, rounded, and/or otherwise angled from the distal end 708a of the sealing surface 706a to a distal end 714a of the wall 712a. In such examples, the curvature of the wall 712a may make it easier to insert the distal end portion 704a into the female connector 50 and to remove the distal end portion 704a from the female connector 50. The distal end 714a of the wall 712a may, in some examples, form at least part of a distal end 716a of the shaft 702a.

The shaft 702a of the bayonet connector 700 may also include a channel 718a of any shape, size, and/or other configuration formed on an outer surface 732a of the shaft 702a. The channel 718a may be formed on the outer surface 732a between the sealing surface 706a and the proximal end portion of the shaft 702a (not shown). Further, the channel 718a may at least partially extend circumferentially around the longitudinal axis 206a. As shown in FIG. 7, the channel 718a may be defined by and/or may otherwise include a distal wall 720a, a proximal wall 722a opposite the distal wall 720a, and a central region 724a extending from the distal wall 720a to the proximal wall 722a. The distal wall 720a may be substantially similar in shape, size, and/or configuration to at least one of the distal walls 306a, 422a described above. For example, the distal wall 720a may comprise a substantially curved, substantially rounded, substantially chamfered, and/or substantially concave sidewall of the channel 718a. In particular, the distal sidewall 720a may include an axial length (as illustrated by at least part of the side profile of the distal sidewall 720a shown in FIG. 7) that extends proximally from the proximal end 710a of the sealing surface 706a to a distal end 726a of the central region 724a. The proximal wall 722a may comprise a substantially curved, substantially rounded, substantially chamfered, substantially concave, and/or substantially convex sidewall of the channel 718a that includes an axial length extending proximally from a proximal end 728a of the central region 724a to a proximal end 730a. In some examples, the proximal wall 722a of the channel 718a may have a configuration that is substantially similar to and/or the same as the distal wall 720a. Additionally, the distal wall 720a may have a radius r' having any desired value. For example, the radius r' may be between approximately 0.1 inch and approximately inches. In further examples, the radius r' may be between approximately 0.5 inches and approximately 5 inches. In still further examples, the radius r' may have a value greater than or less than the values noted above.

Figure 8:
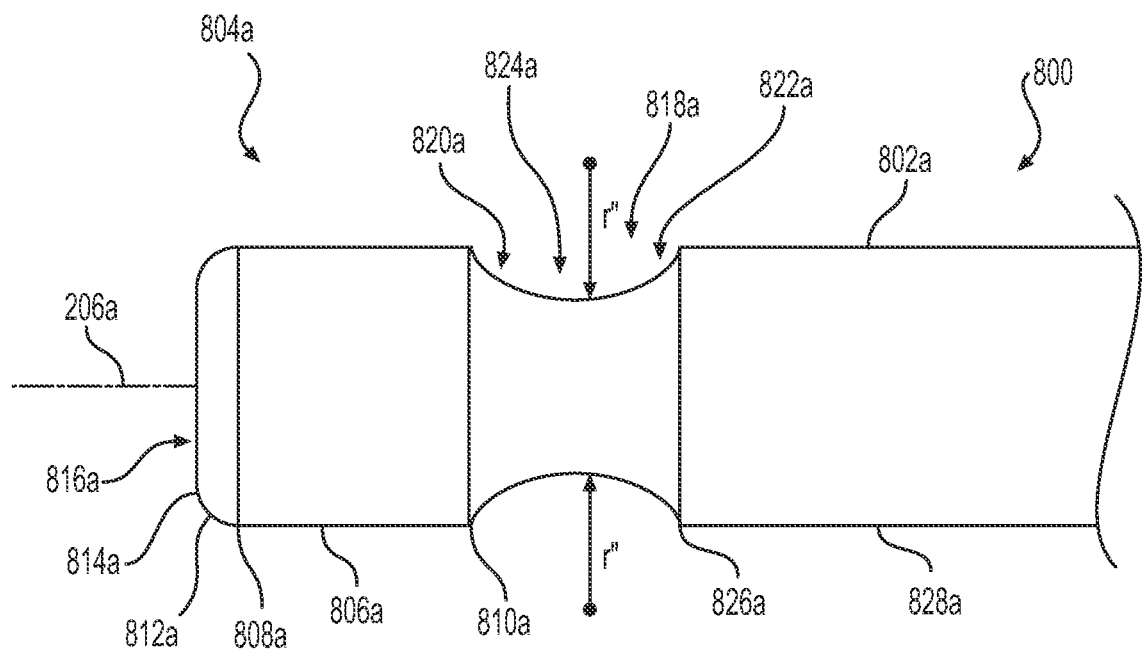
FIG. 8 is a side view of a portion of an example male bayonet connector according to another embodiment of the present disclosure.

FIG. 8 illustrates a portion of still another example bayonet connector 800 and, in particular, a portion of an example shaft 802a thereof. Such an example shaft 802a may include a distal end portion 804a having a sealing surface 806a configured to form a substantially fluid-tight seal with the female connector 50. The sealing surface 706a may have a distal end 808a and a proximal end 810a opposite the distal end 808a. As described above with respect to the bayonet connector 42, the distal end portion 804a may include a wall 812a that is chamfered, curved, tapered, rounded, and/or otherwise angled from the distal end 808a of the sealing surface 806a to a distal end 814a of the wall 812a. In such examples, the curvature of the wall 812a may make it easier to insert the distal end portion 804a into the female connector 50 and to remove the distal end portion 804a from the female connector 50. The distal end 814a of the wall 812a may, in some examples, form at least part of a distal end 816a of the shaft 802a.

The shaft 802a of the bayonet connector 800 may also include a channel 818a of any shape, size, and/or other configuration formed on an outer surface 828a of the shaft 802a. The channel 818a may be formed on the outer surface 828a between the sealing surface 806a and the proximal end portion of the shaft 802a (not shown). Further, the channel 818a may at least partially extend circumferentially around the longitudinal axis 206a. As shown in FIG. 8, the channel 818a may be defined by and/or may otherwise include a distal wall 820a, a proximal wall 822a opposite the distal wall 820a, and a central region 824a extending from the distal wall 820a to the proximal wall 822a. In the example shown in FIG. 8, the channel 818a may comprise a substantially curved, substantially rounded, substantially chamfered, and/or substantially concave annular channel having a substantially uniform radius r" from a distal end of the distal wall 820a to a proximal end 826a of the proximal wall 822a. In such examples, the proximal end 810a of the sealing surface 806a may comprise a distal end of the distal wall 820a, and the substantially uniform radius r" may extend from the proximal end 810a to the proximal end 826a. In particular, the channel 818a may include an axial length (as illustrated by at least part of the side profile of the channel 818a shown in FIG. 8) having a radius r" of any desired value. In some examples, the radius r" may be between approximately 0.1 inch and approximately 10 inches. In further examples, the radius r" may be between approximately 0.5 inches and approximately 5 inches. In still further examples, the radius r" may have a value greater than or less than the values noted above.

Figure 9:
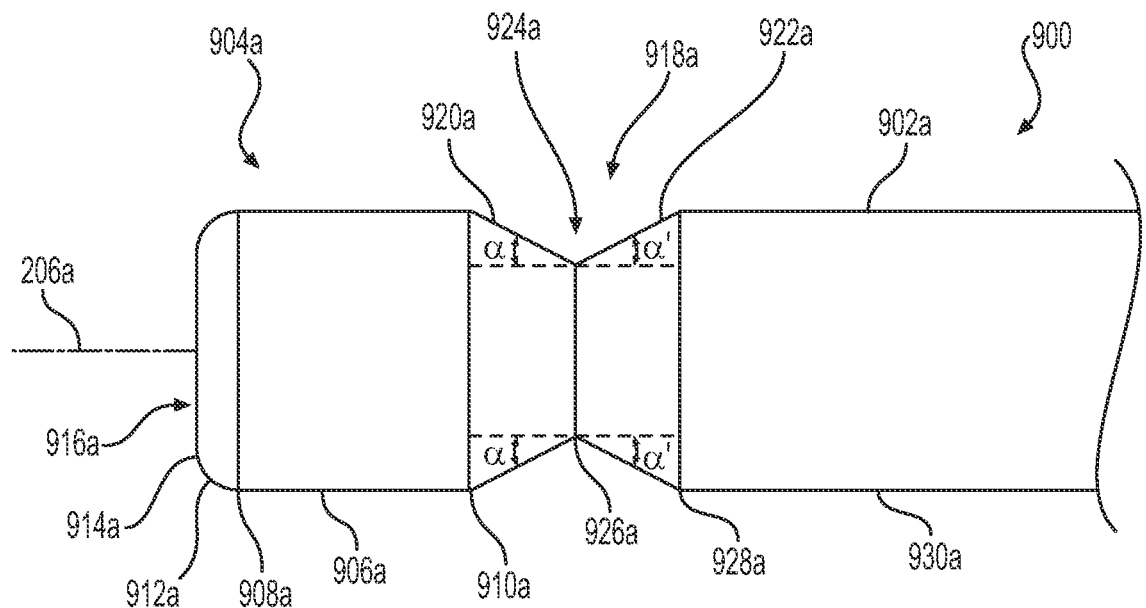
FIG. 9 is a side view of a portion of an example male bayonet connector according to a further embodiment of the present disclosure.

FIG. 9 illustrates a portion of yet another example bayonet connector 900 and, in particular, a portion of an example shaft 902a thereof. Such an example shaft 902a may include a distal end portion 904a having a sealing surface 906a configured to form a substantially fluid-tight seal with the female connector 50. The sealing surface 906a may have a distal end 908a and a proximal end 910a opposite the distal end 908a. As described above with respect to the bayonet connector 42, the distal end portion 904a may include a wall 912a that is chamfered, curved, tapered, rounded, and/or otherwise angled from the distal end 908a of the sealing surface 906a to a distal end 914a of the wall 912a. In such examples, the curvature of the wall 912a may make it easier to insert the distal end portion 904a into the female connector 50 and to remove the distal end portion 904a from the female connector 50. The distal end 914a of the wall 912a may, in some examples, form at least part of a distal end 916a of the shaft 902a.

The shaft 902a of the bayonet connector 900 may also include a channel 918a of any shape, size, and/or other configuration formed on an outer surface 930a of the shaft 902a. The channel 918a may be formed on the outer surface 930a between the sealing surface 906a and the proximal end portion of the shaft 902a (not shown). Further, the channel 918a may at least partially extend circumferentially around the longitudinal axis 206a. As shown in FIG. 9, the channel 918a may be defined by and/or may otherwise include a distal wall 920a, a proximal wall 922a opposite the distal wall 920a, and a central region 924a extending from the distal wall 920a to the proximal wall 922a. In the example shown in FIG. 9, the distal wall 920a may intersect the proximal wall 922 at an apex 926a of the central region 924a. In particular, the channel 918a may comprise an annular channel having a substantially V-shaped profile (as illustrated by at least part of the side profile of the channel 918a shown in FIG. 9). In such examples, the proximal end 910a of the sealing surface 906a may comprise a distal end of the distal wall 920a, and the proximal wall 922a may include a proximal end 928a that mates with the outer surface 930a. The distal wall 920a may extend distally from the apex 926a at an acute angle $\alpha$ relative to the longitudinal axis 206a, and the proximal wall 922a may extend proximally from the apex 926a at an acute angle $\alpha'$ relative to the longitudinal axis 206a. In some examples, the angles $\alpha$, $\alpha'$ may be substantially equal, and in other examples, the angles $\alpha$, $\alpha'$ may have different values. The angles $\alpha$, $\alpha'$ may have any desired value between approximately 0 degrees and approximately 90 degrees.

Figure 10:
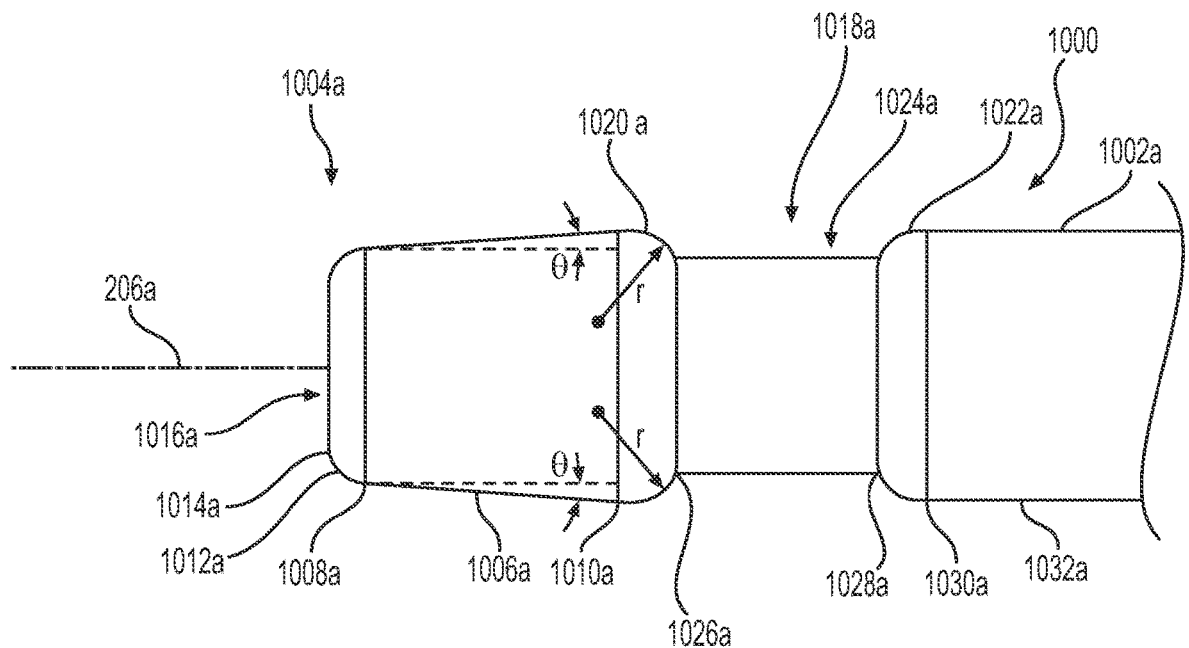
FIG. 10 is a side view of a portion of an example male bayonet connector according to yet another embodiment of the present disclosure.

While the example bayonet connectors described above with respect to at least FIGS. 2-9 include sealing surfaces that have substantially constant diameters, and/or that have respective axial lengths that extend substantially parallel to the longitudinal axes of the shafts defining such sealing surfaces, in further examples, bayonet connectors of the present disclosure may include sealing surfaces that are at least one of curved or disposed at an angle relative to the longitudinal axes of the shafts defining such sealing surfaces. For example, FIG. 10 illustrates a portion of an example bayonet connector 1000 and, in particular, a portion of an example shaft 1002a thereof. Such an example shaft 1002a may include a distal end portion 1004a having a sealing surface 1006a configured to form a substantially fluid-tight seal with the female connector 50. The sealing surface 1006a may have a distal end 1008a and a proximal end 1010a opposite the distal end 1008a. As described above with respect to the bayonet connector 42, the distal end portion 1004a may include a wall 1012a that is chamfered, curved, tapered, rounded, and/or otherwise angled from the distal end 1008a of the sealing surface 1006a to a distal end 1014a of the wall 1012a. In such examples, the curvature of the wall 1012a may make it easier to insert the distal end portion 1004a into the female connector 50 and to remove the distal end portion 1004a from the female connector 50. The distal end 1014a of the wall 1012a may, in some examples, form at least part of a distal end 1016a of the shaft 1002a.

The sealing surface 1006a may include a substantially linear axial length (as illustrated by at least part of the side profile of the sealing surface 1006a shown in FIG. 10) that extends proximally from the distal end 1008a of the sealing surface 1006a to the proximal end 1010a of the sealing surface 1006a. As shown in FIG. 10, such an axial length of the sealing surface 1006a may be disposed at an acute angle $\Theta$ relative to the longitudinal axis 206a, and may extend away from the longitudinal axis 206a from the distal end 1008a of the sealing surface 1006a to the proximal end 1010a. The angle $\Theta$ may have any desired value between approximately 0 degrees and approximately 90 degrees. For example, the angle $\Theta$ may have any desired value between approximately 0 degrees and approximately 15 degrees. In such examples, the distal end 1008a of the sealing surface 1006a (i.e., the distal end of the sealing surface 1006a) may be disposed radially closer to the longitudinal axis 206a than the proximal end 1010a of the sealing surface 1006a (i.e., the proximal end of the sealing surface 1006a).

The shaft 1002a of the bayonet connector 1000 may also include a channel 1018a of any shape, size, and/or other configuration formed on an outer surface 1032a of the shaft 1002a. The channel 1018a may be formed on the outer surface 1032a between the sealing surface 1006a and the proximal end portion of the shaft 1002a (not shown). Further, the channel 1018a may at least partially extend circumferentially around the longitudinal axis 206a. As shown in FIG. 10, the channel 1018a may be defined by and/or may otherwise include a distal wall 1020a, a proximal wall 1022a opposite the distal wall 1020a, and a central region 1024a extending from the distal wall 1020a to the proximal wall 1022a. The distal wall 1020a may be substantially similar in shape, size, and/or configuration to at least one of the distal walls 306a, 422a described above. For example, the distal wall 1020a may comprise a substantially curved, substantially rounded, substantially chamfered, substantially concave, and/or substantially convex sidewall of the channel 1018a. In particular, the distal sidewall 1020a may include an axial length (as illustrated by at least part of the side profile of the distal sidewall 1020a shown in FIG. 10) that extends proximally from the proximal end 1010a of the sealing surface 1006a to a distal end 1026a of the central region 1024a. The proximal wall 1022a may comprise a substantially curved, substantially rounded, substantially chamfered, substantially concave, and/or substantially convex sidewall of the channel 1018a that includes an axial length extending proximally from a proximal end 1028a of the central region 1024a to a proximal end 1030a. In some examples, the proximal wall 1022a of the channel 1018a may have a configuration that is substantially similar to and/or the same as the distal wall 1020a. Additionally, the distal wall 620a may have a radius r having any desired value. For example, similar to the distal wall 620a described above with respect to FIG. 6, the distal wall 1020a and/or the proximal wall 1022a may comprise a substantially convex and/or substantially rounded sidewall having a radius r between approximately inch and approximately 10 inches. In further examples, the radius r of the distal wall 1020a and/or the proximal wall 1022a may be between approximately 0.5 inches and approximately 5 inches. In still further examples, the radius r of the distal wall 1020a and/or the proximal wall 1022a may have a value greater than or less than the values noted above.

Figure 11:
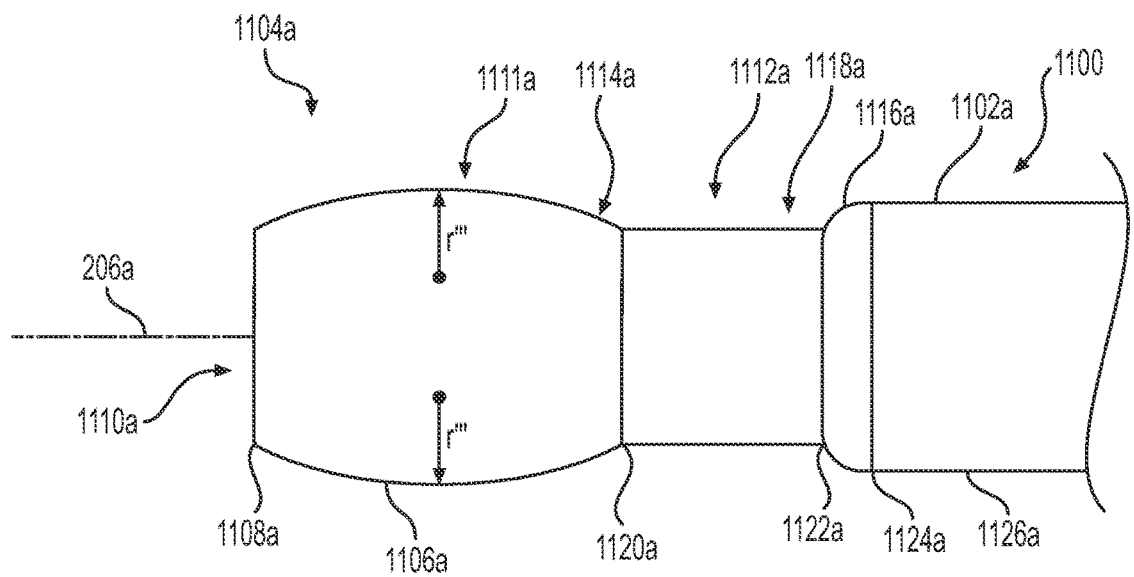
FIG. 11 is a side view of a portion of an example male bayonet connector according to still another embodiment of the present disclosure.

FIG. 11 illustrates a portion of another example bayonet connector 1100 and, in particular, a portion of an example shaft 1102a thereof. Such an example shaft 1102a may include a distal end portion 1104a having a sealing surface 1106a configured to form a substantially fluid-tight seal with the female connector 50. The sealing surface 1106a may have a distal end 1108a and a proximal end 1120a opposite the distal end 1108a. In such examples the distal end 1108a of the sealing surface 1106a may form at least part of a distal end 1110a of the shaft 1102a.

The sealing surface 1106a may include a substantially convex axial length (as illustrated by at least part of the side profile of the sealing surface 1106a shown in FIG. 11) that extends from the distal end 1108a of the sealing surface 1106a to the proximal end 1120a of the sealing surface 1106a. In such examples, the axial length of the sealing surface 1106a may have a substantially constant radius $r'''$ from the distal end 1108a to the proximal end 1120a.

The shaft 1102a of the bayonet connector 1100 may also include a channel 1112a of any shape, size, and/or other configuration formed on an outer surface 1126a of the shaft 1102a. The channel 1112a may be formed on the outer surface 1126a between the sealing surface 1106a and the proximal end portion of the shaft 1102a (not shown). Further, the channel 1112a may at least partially extend circumferentially around the longitudinal axis 206a. As shown in FIG. 11, the channel 1112a may be defined by and/or may otherwise include a distal wall 1114a, a proximal wall 1116a opposite the distal wall 1114a, and a central region 1118a extending from the distal wall 1114a to the proximal wall 1116a. In such examples, the distal wall 1114a may formed, at least in part, by the sealing surface 1106a and may comprise a substantially continuous extension of the sealing surface 1106a. In particular, the distal wall 1114a may terminate at the proximal end 1120a of the sealing surface 1106a. Further, the proximal wall 1116a may comprise a substantially curved, substantially rounded, substantially chamfered, substantially concave, and/or substantially convex sidewall of the channel 1112a that includes an axial length extending proximally from a proximal end 1122a of the central region 1118a to a proximal end 1124a. In some examples, the proximal wall 1116a of the channel 1112a may have a configuration that is substantially similar to and/or the same as, for example, the proximal wall 622a described above with respect to FIG. 6.

Figure 12:
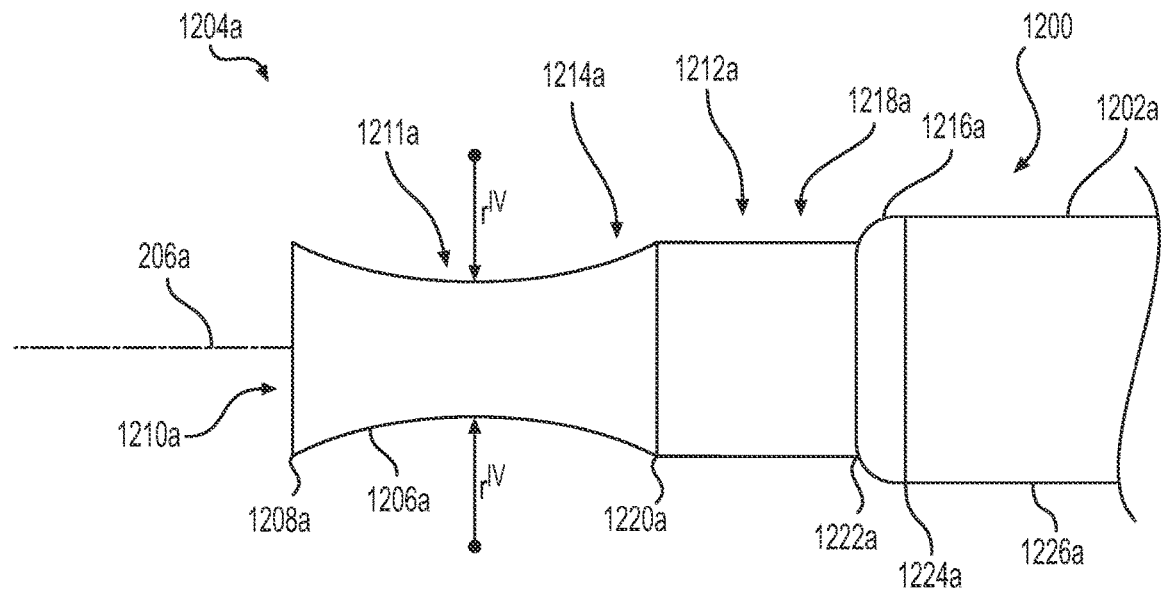
FIG. 12 is a side view of a portion of an example male bayonet connector according to a further embodiment of the present disclosure.

FIG. 12 illustrates a portion of yet another example bayonet connector 1200 and, in particular, a portion of an example shaft 1202a thereof. Such an example shaft 1202a may include a distal end portion 1204a having a sealing surface 1206a configured to form a substantially fluid-tight seal with the female connector 50. The sealing surface 1206a may have a distal end 1208a and a proximal end 1220a opposite the distal end 1208a. In such examples the distal end 1208a of the sealing surface 1206a may form at least part of a distal end 1210a of the shaft 1202a.

The sealing surface 1206a may include a substantially concave axial length (as illustrated by at least part of the side profile of the sealing surface 1206a shown in FIG. 12) that extends from the distal end 1208a of the sealing surface 1206a to the proximal end 1220a of the sealing surface 1206a. In such examples, the axial length of the sealing surface 1206a may have a substantially constant radius $r^{iv}$ from the distal end 1208a to the proximal end 1220a. In particular, the sealing surface 1206a may include a central region 1211a that is characterized at least in part by the radius $r^{iv}$ having any desired value. For example, the central region 1211a may be radially closer to the longitudinal axis 206a than at least one of the proximal end 1220a or the distal end 1208a. In some examples, the radius $r^{iv}$ may have a value between approximately 0.1 inch and approximately 10 inches. In further examples, the radius $r^{iv}$ may have a value greater than or less than the values noted above.

The shaft 1202a of the bayonet connector 1200 may also include a channel 1212a of any shape, size, and/or other configuration formed on an outer surface 1226a of the shaft 1202a. The channel 1212a may be formed on the outer surface 1226a between the sealing surface 1206a and the proximal end portion of the shaft 1202a (not shown). Further, the channel 1212a may at least partially extend circumferentially around the longitudinal axis 206a. As shown in FIG. 12, the channel 1212a may be defined by and/or may otherwise include a distal wall 1214a, a proximal wall 1216a opposite the distal wall 1214a, and a central region 1218a extending from the distal wall 1214a to the proximal wall 1216a. In such examples, the distal wall 1214a may formed, at least in part, by the substantially concave sealing surface 1206a and may comprise a substantially continuous extension of the sealing surface 1206a. In particular, the distal wall 1214a may terminate at the proximal end 1220a of the sealing surface 1206a. Further, the proximal wall 1216a may comprise a substantially curved, substantially rounded, substantially chamfered, substantially concave, and/or substantially convex sidewall of the channel 1212a that includes an axial length extending proximally from a proximal end 1222a of the central region 1218a to a proximal end 1224a. In some examples, the proximal wall 1216a of the channel 1212a may have a configuration that is substantially similar to and/or the same as, for example, the proximal wall 622a described above with respect to FIG. 6.

Figure 13:
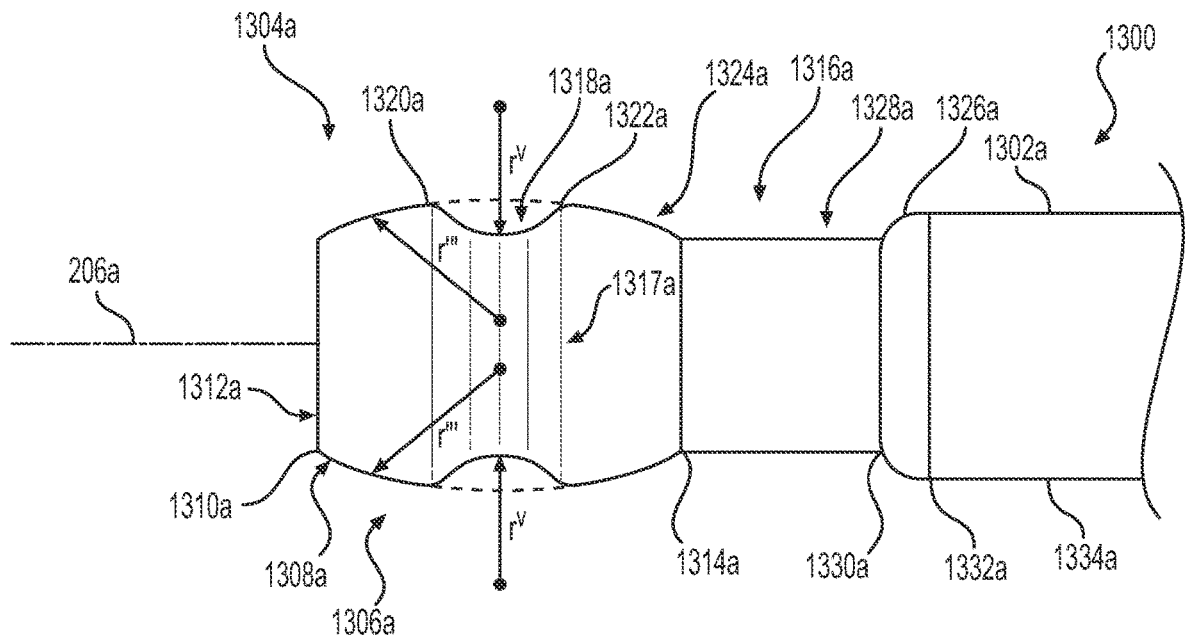
FIG. 13 is a side view of a portion of an example male bayonet connector according to yet another embodiment of the present disclosure.

FIG. 13 illustrates a portion of a further example bayonet connector 1300 and, in particular, a portion of an example shaft 1302a thereof. The bayonet connector 1300 is similar in some respects to the bayonet connector 1100 described above with respect to FIG. 11. For example, the shaft 1302a of the bayonet connector 1300 may include a distal end portion 1304a having a sealing surface 1306a configured to form a substantially fluid-tight seal with the female connector 50. The sealing surface 1306a may be substantially rounded, substantially curved, substantially tapered, substantially concave, and/or substantially convex in shape, and may include, for example, a substantially convex axial length 1308a. The sealing surface 1306a may also include a distal end 1310a, and the distal end 1310a may form at least part of a distal end 1312a of the shaft 1302a. The sealing surface 1306 may also include a proximal end 1314a opposite the distal end 1310a.

As illustrated by at least part of the side profile of the sealing surface 1306a shown in FIG. 13, the axial length 1308a may extend, at least partially, from the distal end 1310a of the sealing surface 1306a to the proximal end 1314a of the sealing surface 1306a. In such examples, one or more portions of the axial length 1308a of the sealing surface 1306a (e.g., a distal portion and a proximal portion thereof) may have a substantially constant radius r''' similar to the radius r''' described above with respect to FIG. 11. The example axial length 1308a of the sealing surface 1306a is shown in phantom (e.g., with dashed lines) between the distal portion and the proximal portion thereof. The example sealing surface 1306a may also include an annular central region 1317a disposed between the distal end 1310a and the proximal end 1314a. Such an annular central region 1317a may extend substantially circumferentially around the longitudinal axis 206a, and may be substantially rounded, substantially curved, substantially tapered, substantially concave, and/or substantially convex in shape. In some examples, the annular central region 1317a may be disposed substantially centrally along the sealing surface 1306a, and may be configured to mate with an O-ring, gasket, seal, or other component of the female connector 50. The annular central region 1317a may include, for example, a substantially concave axial length 1318a (as shown by the side profile of the axial length 1318a illustrated in FIG. 13) having a distal end 1320a and a proximal end 1322a opposite the distal end 1320a. In some examples, the concave axial length 1318a may be defined by a substantially constant radius $r^v$ extending from the distal end 1320a to the proximal end 1322a and having any desired value. For example, the radius $r^v$ may have a value between approximately 0.1 inch and approximately 10 inches. In further examples, the radius $r^v$ may have a value greater than or less than the values noted above.

The shaft 1302a of the bayonet connector 1300 may also include a channel 1316a of any shape, size, and/or other configuration formed on an outer surface 1334a of the shaft 1302a. The channel 1316a may be formed on the outer surface 1334a between the sealing surface 1306a and the proximal end portion of the shaft 1302a (not shown). Further, the channel 1316a may at least partially extend circumferentially around the longitudinal axis 206a. As shown in FIG. 13, the channel 1316a may be defined by and/or may otherwise include a distal wall 1324a, a proximal wall 1326a opposite the distal wall 1324a, and a central region 1328a extending from the distal wall 1324a to the proximal wall 1326a. In such examples, the distal wall 1324a may formed, at least in part, by the sealing surface 1306a and may comprise a substantially continuous extension of the sealing surface 1306a. In particular, the distal wall 1324a may terminate at the proximal end 1314a of the sealing surface 1306a. Further, the proximal wall 1326a may comprise a substantially curved, substantially rounded, substantially chamfered, substantially concave, and/or substantially convex sidewall of the channel 1316a that includes an axial length extending proximally from a proximal end 1330a of the central region 1328a to a proximal end 1332a. In some examples, the proximal wall 1326a of the channel 1316a may have a configuration that is substantially similar to and/or the same as, for example, the proximal wall 622a described above with respect to FIG. 6.

Figure 14:
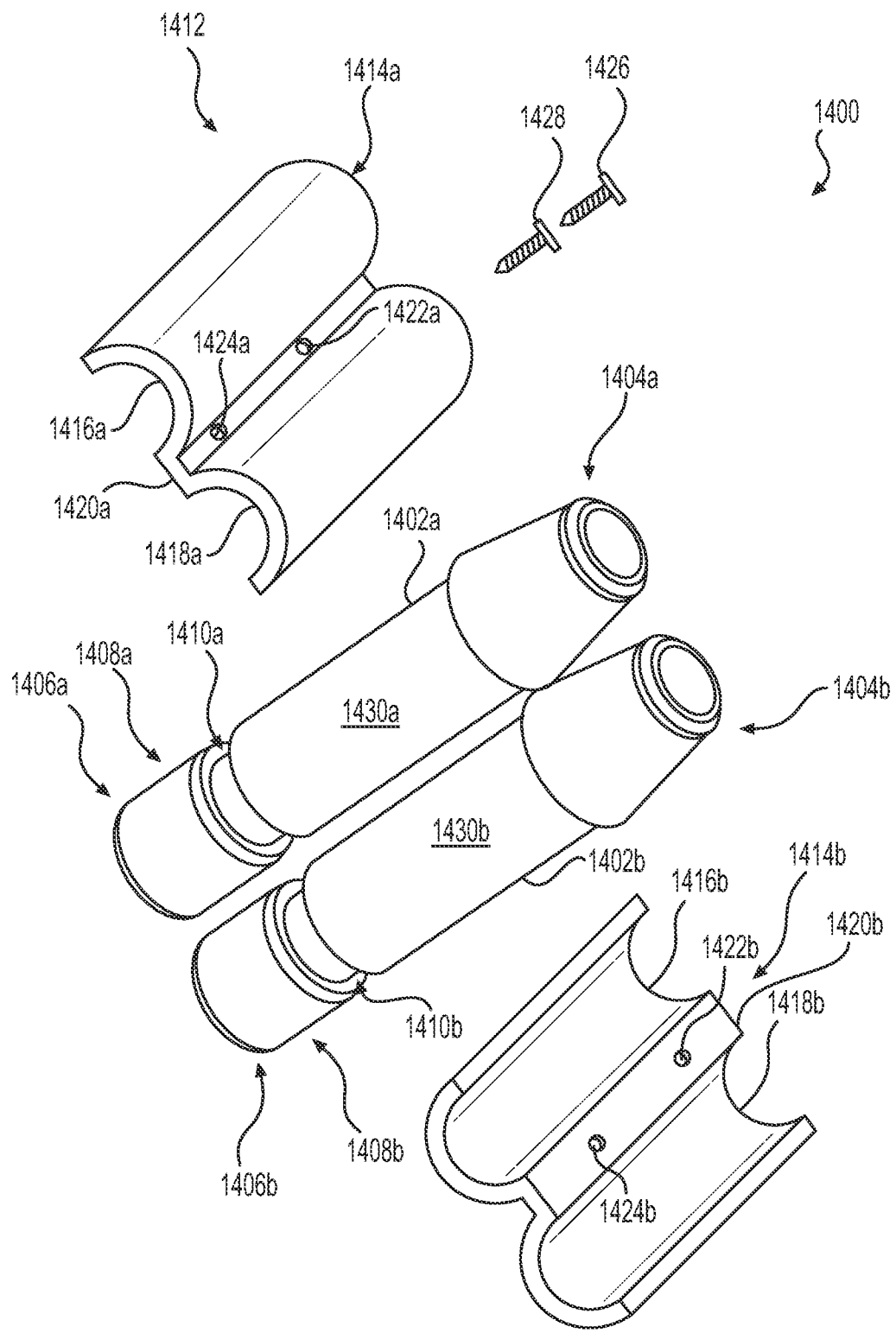
FIG. 14 is an exploded view of a male bayonet connector including a connector according to an example embodiment of the present disclosure.

In still further embodiments of the present disclosure, an example bayonet connector may comprise two or more separate shafts that can be releasably connected together by various means. For example, as shown in FIG. 14 an example bayonet connector 1400 may include a first shaft 1402a and a second shaft 1402b that is substantially similar to and/or the same as the first shaft 1402a. The first shaft 1402a may include a proximal end portion 1404a, and a distal end portion 1406a having a sealing surface 1408a configured to form a substantially fluid-tight seal with the female connector 50. As shown in FIG. 14, the proximal end portion 1404a may be disposed opposite the distal end portion 1406a. Similarly, the second shaft 1402b may include a proximal end portion 1404b, and a distal end portion 1406b having a sealing surface 1408b configured to form a substantially fluid-tight seal with the female connector 50. The first and second shafts 1402a, 1402b may include respective lumens extending substantially along respective longitudinal axes (not shown) of the shafts 1402a, 1402b from the respective distal end portions 1406a, 1406b to the respective proximal end portions 1404a, 1404b. The first and second shafts 1402a, 1402b may also include respective channels 1410a, 1410b formed on respective outer surfaces 1430a, 1430b of the shafts 1402a, 1402b. The respective channels 1410a, 1410b may be disposed between the respective sealing surfaces 1408a, 1408b and the respective proximal end portions 1404a, 1404b. Additionally, the respective channels 1410a, 1410b may at least partially extend circumferentially around the respective longitudinal axes of the first and second shafts 1402a, 1402b.

The bayonet connector 1400 may also include a connector 1412 detachably connecting the first shaft 1402a with the second shaft 1402b. For example, the connector 1412 may comprise a bracket having a first half 1414a and a second half 1414b disposed opposite the first half 1414a. In such examples, the first half 1414a may be detachably connected to the second half 1414b. The first half 1414a may extend at least partially circumferentially around the outer surface 1430a of the first shaft 1402a, and may also extend at least partially circumferentially around the outer surface 1430b of the second shaft 1402b. Similarly, the second half 1414b may extend at least partially circumferentially around the outer surface 1430a of the first shaft 1402a, and may also extend at least partially circumferentially around the outer surface 1430b of the second shaft 1402b. The first half 1414a of the connector 1412 may, for example, include substantially concave first and second inner surfaces 1416a, 1418a extending longitudinally along a length of the first half 1414a and configured to mate with the respective outer surfaces 1430a, 1430b. The first half 1414a may also include a central region 1420a spacing the first inner surface 1416a from the second inner surface 1418a. As shown in FIG. 14, the central region 1420a may define one or more thru holes 1422a, 1424a configured to accept respective bolts, screws, weldments, pins, or other connection components 1426, 1428. In such examples, the one or more connection components 1426, 1428 may be configured to detachably connect the first half 1414a with the second half 1414b when the first and second shafts 1402a, 1402b are disposed between the first and second halves 1414a, 1414b. Similarly, the second half 1414b of the connector 1412 may include substantially concave first and second inner surfaces 1416b, 1418b extending longitudinally along a length of the second half 1414b and configured to mate with the respective outer surfaces 1430a, 1430b. The second half 1414b may also include a central region 1420b spacing the first inner surface 1416b from the second inner surface 1418b. As shown in FIG. 14, the central region 1420b may define one or more thru holes 1422b, 1424b configured to accept the connection components 1426, 1428 described above.

Figure 15:
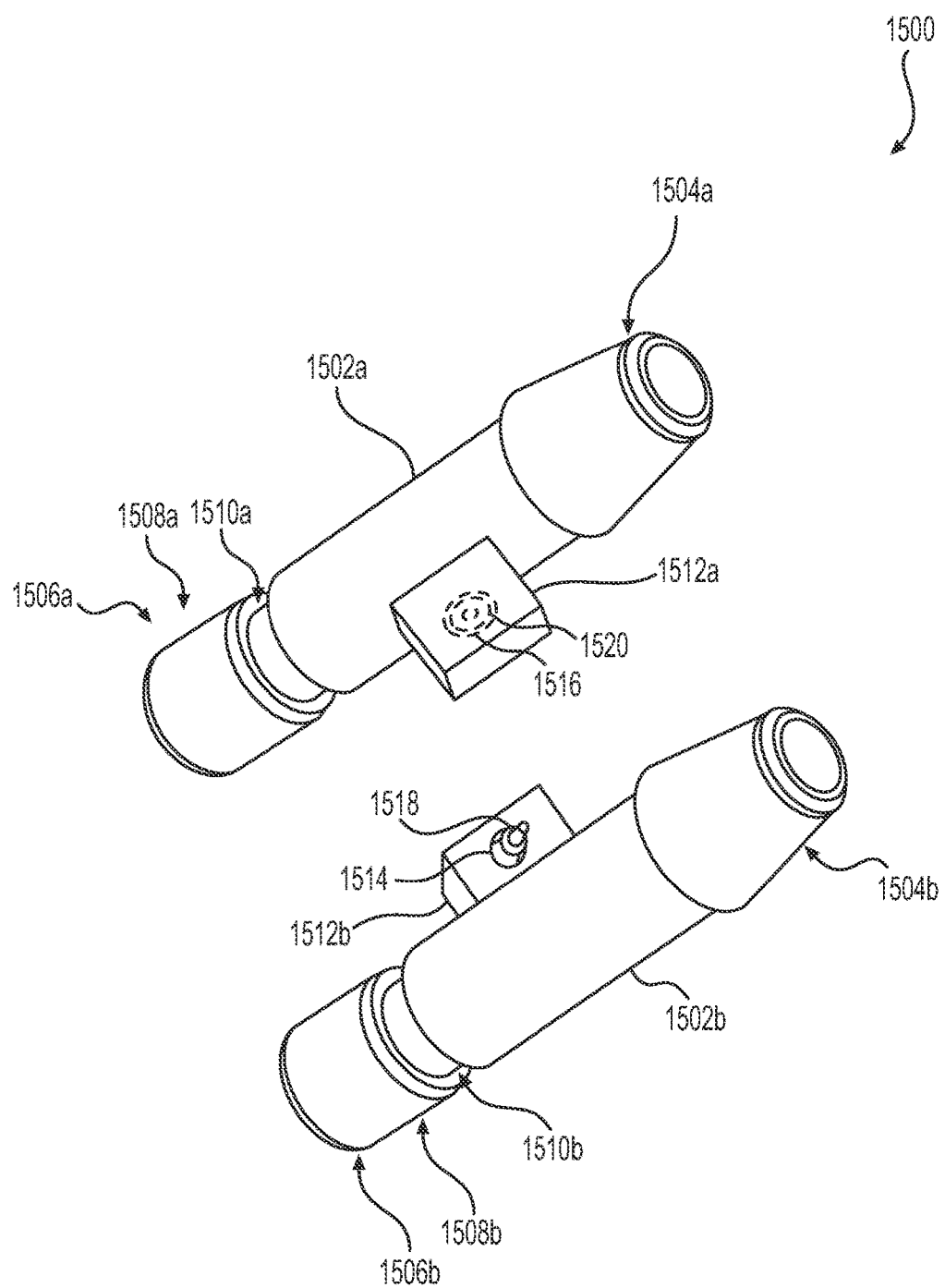
FIG. 15 is an exploded view of a male bayonet connector including a connector according to another example embodiment of the present disclosure.

FIG. 15 illustrates another example bayonet connector 1500 of the present disclosure. Similar to the bayonet connector 1400 described above with respect to FIG. 14, the bayonet connector 1500 may include a first shaft 1502a and a second shaft 1502b that is substantially similar to and/or the same as the first shaft 1502a. The first shaft 1502a may include a proximal end portion 1504a, and a distal end portion 1506a having a sealing surface 1508a configured to form a substantially fluid-tight seal with the female connector 50. As shown in FIG. 15, the proximal end portion 1504a may be disposed opposite the distal end portion 1506a. Similarly, the second shaft 1502b may include a proximal end portion 1504b, and a distal end portion 1506b having a sealing surface 1508b configured to form a substantially fluid-tight seal with the female connector 50. The first and second shafts 1502a, 1502b may include respective lumens extending substantially along respective longitudinal axes (not shown) of the shafts 1502a, 1502b from the respective distal end portions 1506a, 1506b to the respective proximal end portions 1504a, 1504b. The first and second shafts 1502a, 1502b may also include respective channels 1510a, 1510b formed on respective outer surfaces of the shafts 1502a, 1502b. The respective channels 1510a, 1510b may be disposed between the respective sealing surfaces 1508a, 1508b and the respective proximal end portions 1504a, 1504b. Additionally, the respective channels 1510a, 1510b may at least partially extend circumferentially around the respective longitudinal axes of the first and second shafts 1502a, 1502b.

The bayonet connector 1500 may also include a connector detachably connecting the first shaft 1502a with the second shaft 1502b. For example, the connector of the example bayonet connector 1500 may comprise a first tab 1512a extending radially from the outer surface of the first shaft 1502a, and a second tab 1512b extending radially from the outer surface of the second shaft 1502b. In such examples, the first tab 1512a may be detachably connected to the second tab 1512b, and such a connection may detachably connect the first shaft 1502a with the second shaft 1502b. To facilitate such a connection, one of the first tab 1512a or the second tab 1512b may include a pin, shaft, or other such extension 1514, and the other of the first tab 1512a or the second tab 1512b may include a corresponding orifice 1516 configured to at least temporarily mate with the extension 1514. In some examples, the extension 1514 may include one or more ridges, nubs, flanges, rims, hooks, or other features 1518 configured to assist in forming a snap fit, pressed fit, or other detachable connection with the orifice 1516. In such examples, the orifice 1516 may include one or more corresponding slots, grooves, channels, coves, and/or other features 1520 configured to accept the feature(s) 1518 of the extension 1514.

Figure 16:
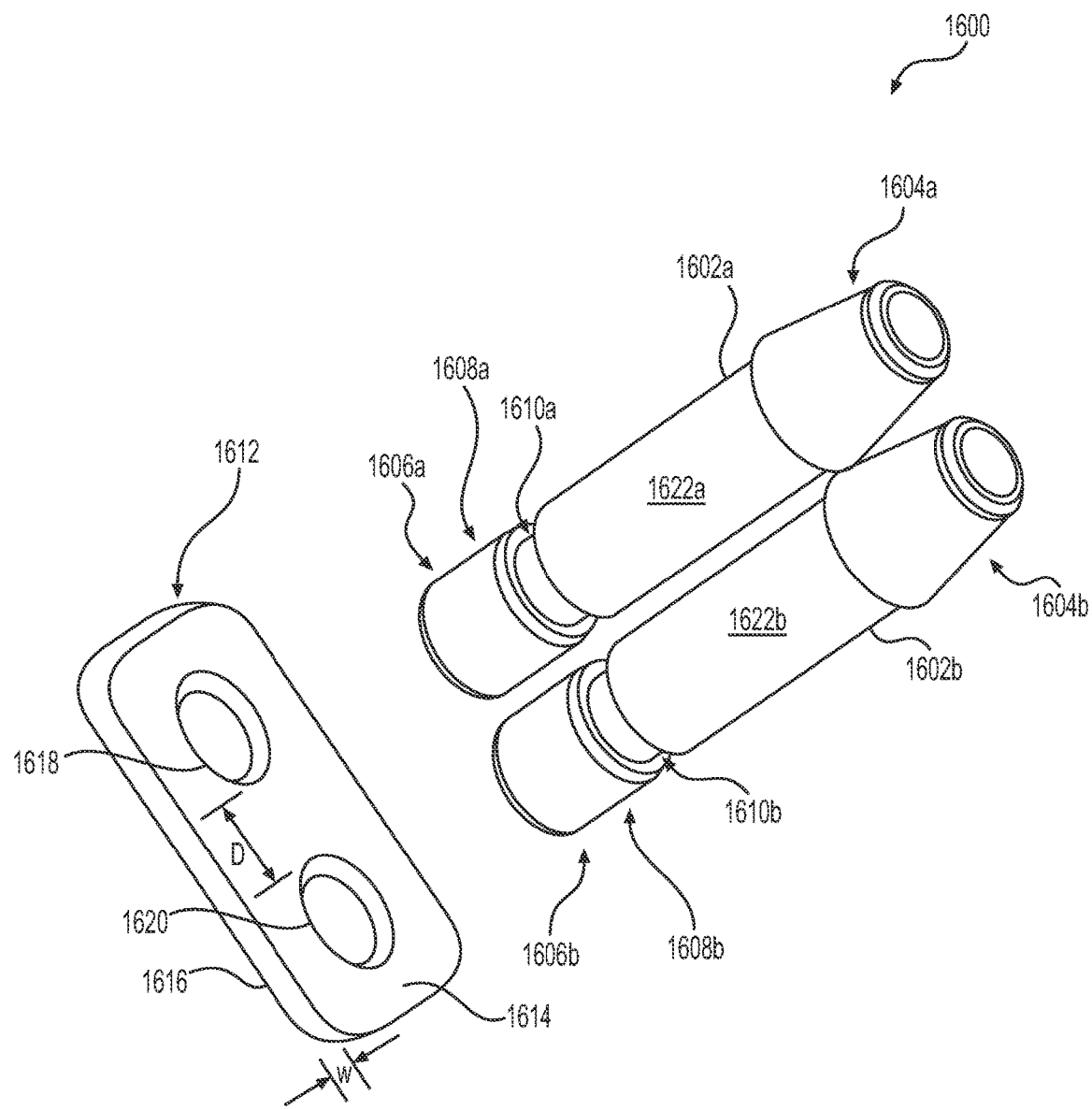
FIG. 16 is an exploded view of a male bayonet connector including a connector according to a further example embodiment of the present disclosure.

FIG. 16 illustrates yet another example bayonet connector 1600 of the present disclosure. Similar to the bayonet connector 1400 described above with respect to FIG. 14, the bayonet connector 1600 may include a first shaft 1602a and a second shaft 1602b that is substantially similar to and/or the same as the first shaft 1602a. The first shaft 1602a may include a proximal end portion 1604a, and a distal end portion 1606a having a sealing surface 1608a configured to form a substantially fluid-tight seal with the female connector 50. As shown in FIG. 16, the proximal end portion 1604a may be disposed opposite the distal end portion 1606a. Similarly, the second shaft 1602b may include a proximal end portion 1604b, and a distal end portion 1606b having a sealing surface 1608b configured to form a substantially fluid-tight seal with the female connector 50. The first and second shafts 1602a, 1602b may include respective lumens extending substantially along respective longitudinal axes (not shown) of the shafts 1602a, 1602b from the respective distal end portions 1606a, 1606b to the respective proximal end portions 1604a, 1604b. The first and second shafts 1602a, 1602b may also include respective channels 1610a, 1610b formed on respective outer surfaces 1622a, 1622b of the shafts 1602a, 1602b. The respective channels 1610a, 1610b may be disposed between the respective sealing surfaces 1608a, 1608b and the respective proximal end portions 1604a, 1604b. Additionally, the respective channels 1610a, 1610b may at least partially extend circumferentially around the respective longitudinal axes of the first and second shafts 1602a, 1602b.

The bayonet connector 1600 may also include a connector 1612 detachably connecting the first shaft 1602a with the second shaft 1602b. For example, the connector 1612 of the example bayonet connector 1600 may comprise a bracket, plate, or other like structure having a first surface 1614 and a second surface 1616 opposite the first surface 1614. The connector 1612 may also have a width W extending from the first surface 1614 to the second surface 1616. The connector 1612 may further include a first thru hole 1618 and a second thru hole 1620 spaced from the first thru hole 1618. For example, an outer diameter and/or circumference of the first thru hole 1618 may be spaced from a corresponding outer diameter and/or circumference of the second thru hole 1620 by a distance D along the first surface 1614. In such examples, the first and second thru holes 1618, 1620 may have any shape size, diameter, and/or other configuration useful in detachably connecting the first shaft 1602a with the second shaft 1602b. For example, the first thru hole 1618 may have a diameter that is substantially equal to a corresponding diameter of the outer surface 1622a of the first shaft 1602a. Similarly, the second thru hole 1620 may have a diameter that is substantially equal to a corresponding diameter of the outer surface 1622b of the second shaft

1602b. Additionally, the connector 1612 may be made from plastic, rubber, polymeric material, and/or any other relatively flexible material in order to assist in detachably connecting the first shaft 1602a with the second shaft 1602b. For example, the first thru hole 1618 may be shaped, sized, and/or otherwise configured to form a pressed fit with the outer surface 1622a of the first shaft 1602a, and the second thru hole 1620 may be shaped, sized, and/or otherwise configured to form a pressed fit with the outer surface 1622b of the second shaft 1602b.

Figure 17:
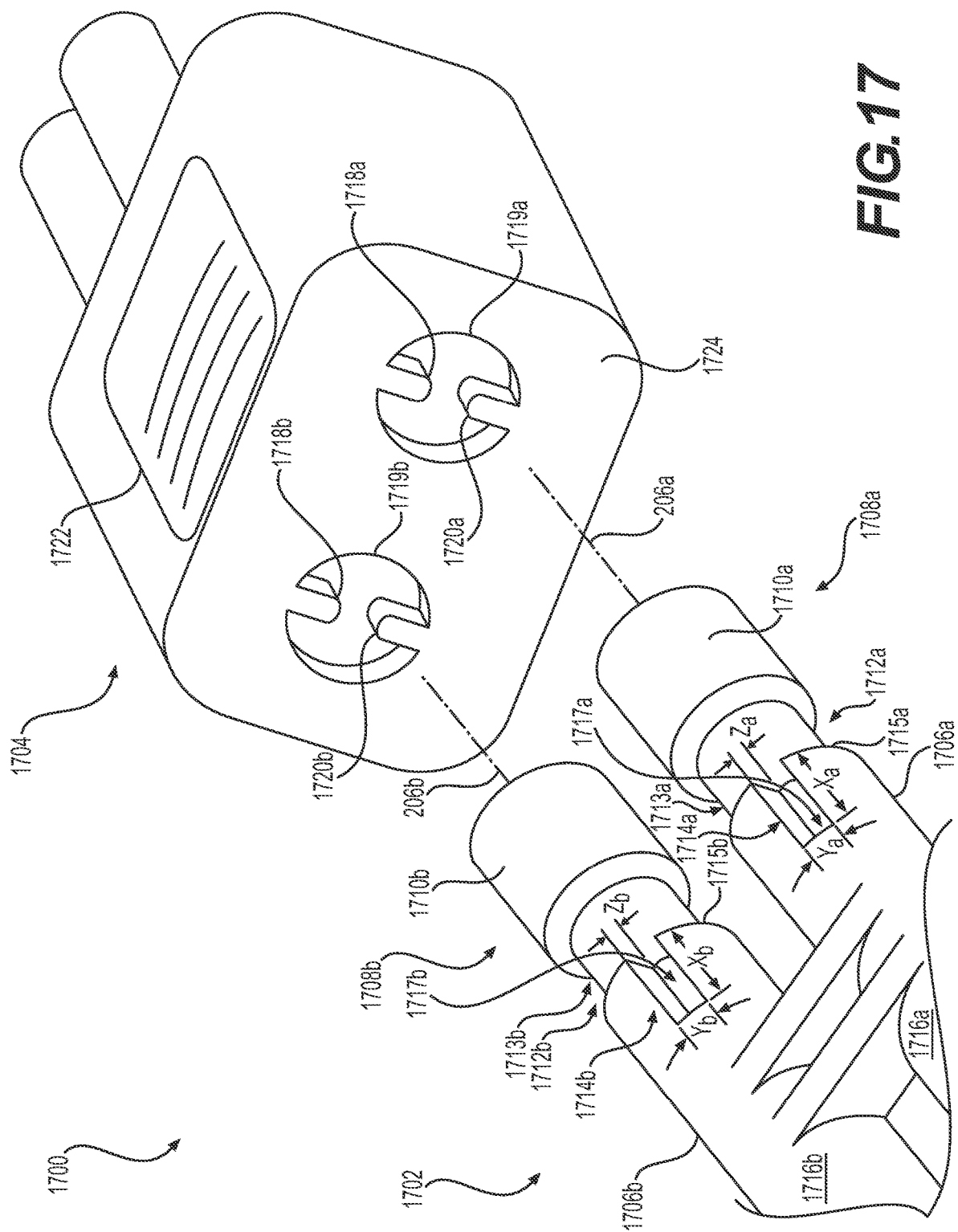
FIG. 17 is a partial isometric view of a portion of a male bayonet connector and a female connector according to another example embodiment of the present disclosure.
Figure 18:
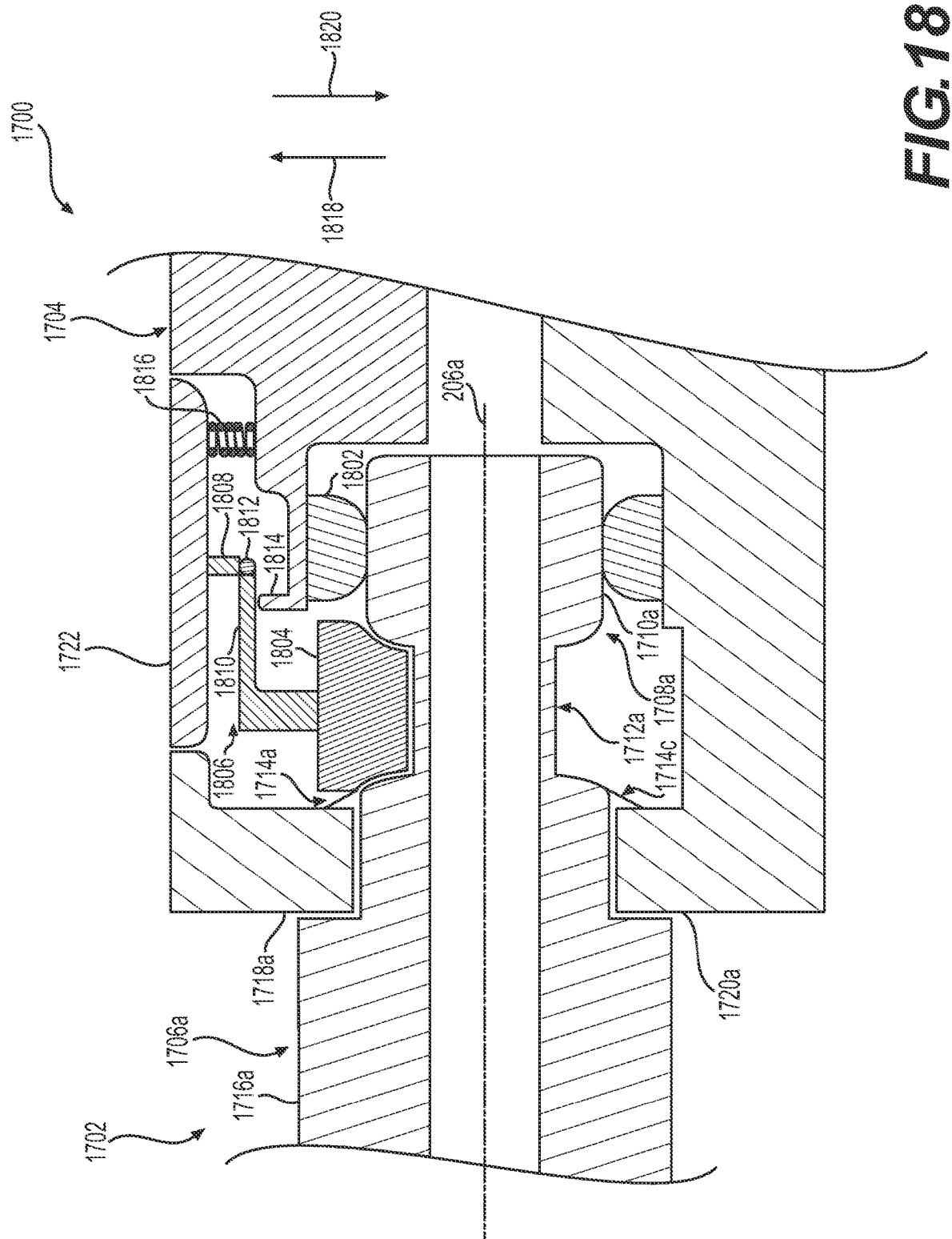
FIG. 18 is a partial cross-sectional view of the male bayonet connector and female connector shown in FIG. 17.

In still further example embodiments of the present disclosure, a male bayonet connector may include one or more structures configured to assist in aligning the bayonet connector as at least a portion thereof is inserted into an example female connector, and/or stabilizing the male bayonet connector once at least a portion of the male bayonet connector is inserted into such a female connector. For instance, FIGS. 17 and 18 illustrate an example system 1700 of the present disclosure in which a male bayonet connector 1702 includes one or more channels, grooves, orifices, notches, or other female structures configured to accept a corresponding pin, leg, shaft, finger, ridge, extension, or other male feature of a female connector 1704. For example, as shown in at least FIG. 17, a male bayonet connector 1702 may include a first shaft 1706a, and a second shaft 1706b coupled to the first shaft 1706b. The first shaft 1706a may include a distal end portion 1708a having a sealing surface 1710a configured to form a substantially fluid-tight seal with the female connector 1704. Additionally, the second shaft 1706b may include a distal end portion 1708b having a respective sealing surface 1710b configured to form a substantially fluid-tight seal with the female connector 1704. The first shaft 1706a may also include at least one channel 1712a disposed between the sealing surface 1710a and a proximal end portion of the first shaft 1706a. Similarly, the second shaft 1706b may include at least one channel 1712b disposed between the sealing surface 1710b and a proximal end portion of the second shaft 1706b. The channel 1712a may extend at least partially circumferentially around the longitudinal axis 206a of the first shaft 1706a, and the channel 1712b may extend at least partially circumferentially around the longitudinal axis 206b of the second shaft 1706b. As explained with respect to various other embodiments of the present disclosure, the channel 1712a may be at least partly defined by a central region 1713a and a proximal wall 1715a, and at least part of such a proximal wall 1715a may extend radially from the central region 1713a of the channel 1712a to an outer surface 1716a of the shaft 1706a. Likewise, the channel 1712b of the shaft 1706b may be at least partly defined by a central region 1713b and a proximal wall 1715b, and at least part of such a proximal wall 1715b may extend radially from the central region 1713b of the channel 1712b to an outer surface 1716b of the shaft 1706b.

As shown in FIG. 17, the shaft 1706a may also include at least one axial groove 1714a oriented substantially parallel to the longitudinal axis 206a of the shaft 1706a. The axial groove 1714a may extend proximally from, for example, the central region 1713a and/or the proximal wall 1715a of the channel 1712a. For example, the axial groove 1714a may include a length Xa extending proximally from the proximal wall 1715a of the channel 1712a to a proximal end 1717a of the axial groove 1714a. The axial groove 1714a may also include a width Ya extending circumferentially about the longitudinal axis 206a. The axial groove 1714a may further include a depth Za extending from the outer surface 1716a of the shaft 1706a substantially toward the longitudinal axis 206a. Similarly, the shaft 1706b may include at least one axial groove 1714b oriented substantially parallel to the longitudinal axis 206b of the shaft 1706b. The axial groove 1714b may extend proximally from, for example, the central region 1713b and/or the proximal wall 1715b of the channel 1712b. For example, the axial groove 1714b may include a length Xb extending proximally from the proximal wall 1715b of the channel 1712b to a proximal end 1717b of the axial groove 1714b. The axial groove 1714b may also include a width Yb extending circumferentially about the longitudinal axis 206b. The axial groove 1714b may further include a depth Zb extending from the outer surface 1716b of the shaft 1706b substantially toward the longitudinal axis 206b.

The one or more respective axial grooves 1714a, 1714b of the shafts 1706a, 1706b may be configured to mate with and/or accept at least a portion of the female connector 1704 when at least part of the bayonet connector 1702 is inserted into the female connector 1704. For example, the female connector 1704 may include a first orifice 1719a configured to accept passage of at least part of the distal end portion 1708a therethrough, and a second orifice 1719b configured to accept passage of at least part of the distal end portion 1708b therethrough. The orifice 1719a may include at least one extension 1718a, and the extension may be configured to mate with the first axial groove 1714a when the sealing surface 1710a of the first shaft 1706a forms a substantially fluid-tight seal with the female connector 1704. It is understood that in examples in which the first shaft 1706a includes one or more additional axial grooves, the female connector 1704 may also include one or more corresponding extensions 1720a configured to mate with such additional axial grooves as noted above with respect to the extension 1718a.

As shown in FIG. 17, the second orifice 1719b may be spaced from the first orifice 1719a. In such examples, the second orifice 1719b may include at least one extension 1718b, and the extension 1718b may be configured to mate with the second axial groove 1714b when the sealing surface 1710b of the first shaft 1706b forms a substantially fluid-tight seal with the female connector 1704. It is understood that in examples in which the second shaft 1706b includes one or more additional axial grooves, the female connector 1704 may also include one or more corresponding extensions 1720b configured to mate with such additional axial grooves as noted above with respect to the extension 1718b. The female connector 1704 may also include one or more buttons, levers, biased members, or other like actuators 1722 configured to temporarily and/or releasably lock the male bayonet connector 1702 in a substantially stationary position relative to the female connector 1704 when the sealing surfaces 1710a, 170b form respective substantially fluid-tight seals with the female connector 1704. In such examples, the at least part of the proximal wall 1715a and/or at least part of the proximal wall 1715b may substantially abut an outer wall 1724 of the female connector when the sealing surfaces 1710a, 170b form respective substantially fluid-tight seals with the female connector 1704.

FIG. 18 illustrates the bayonet connector 1702 mated with the female connector 1704. As shown in FIG. 18, at least the first shaft 1706a may include a first axial groove 1714a, and a substantially similar additional axial groove 1714c disposed opposite the axial groove 1714a. FIG. 18 also illustrates example structures of the female connector 1704 in greater detail. For example, the female connector 1704 may one or more O-rings, gaskets, washers, or other sealing structures 1802 configured to mate with and form respective substantially fluid-tight seals with the first shaft 1706a and the second shaft 1706. In particular, such sealing structures 1802 may be positioned within the female connector 1704 and/or otherwise shaped, sized, or configured to form respective substantially fluid-tight seals with the first sealing surface 1710a and with the second sealing surface 1710b.

The female connector 1704 may also include one or more additional structures disposed within an internal space 1806 of the connector 1704 and configured to selectively engage with the bayonet connector 1702. For example, the female connector 1704 may include a plunger 1804 connected to the actuator 1722 via one or more linkages 1808, 1810. In some examples, a first linkage 1808 may be coupled to the actuator 1722, and the first linkage 1808 may also be coupled to the second linkage 1810 via one or more hinges 1812 or other like structures. In such examples, the hinge 1812 may comprise a spring-loaded and/or otherwise biased hinge. Alternatively, the female connector 1704 may include one or more separate springs or other biasing members 1816 configured to bias the actuator 1722 in the direction of arrow 1818. When a force is applied to the actuator 1722 in, for example, the direction of arrow 1820, the linkages 1808, 1810, the hinge 1812, and/or the biasing member 1816 may cause the plunger 1804 to move in the direction of arrow 1818, thereby enabling the bayonet connector 1704 to be released from the female connector 1704. The female connector 1704 may further include one or more stands 1814 configured to assist in cantilevering, for example, the linkage 1810 and/or to otherwise assist in facilitating movement of the plunger 1804 relative to the bayonet connector 1702.

Figure 19:
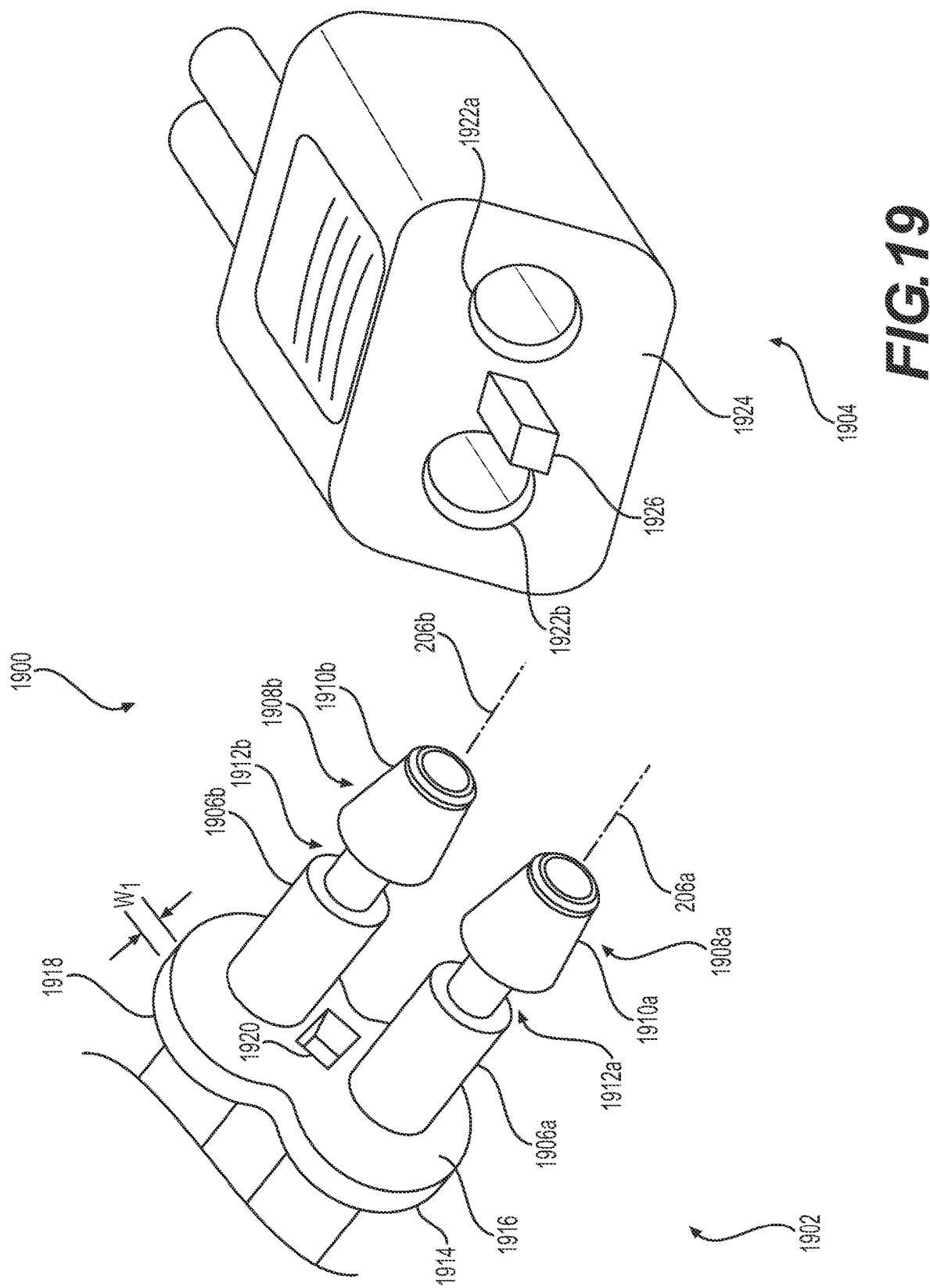
FIG. 19 is a partial isometric view of a portion of a male bayonet connector and a female connector according to still another example embodiment of the present disclosure.

FIG. 19 illustrates still another example system 1900 of the present disclosure including one or more components configured to assist in aligning the male bayonet connector as at least a portion thereof is inserted into an example female connector, and/or stabilizing the male bayonet connector once at least a portion of the male bayonet connector is inserted into such a female connector. As shown in FIG. 19, an example male bayonet connector may include an intermediate linkage having one or more channels, grooves, orifices, notches, thru holes, or other female structures configured to accept a corresponding pin, leg, shaft, finger, ridge, extension, or other male feature of a female connector 1904. For example, as shown in FIG. 19, a male bayonet connector 1902 may include a first shaft 1906a, and a second shaft 1906b coupled to the first shaft 1906b. The first shaft 1906a may include a distal end portion 1908a having a sealing surface 1910a configured to form a substantially fluid-tight seal with the female connector 1904. Additionally, the second shaft 1906b may include a distal end portion 1908b having a respective sealing surface 1910b configured to form a substantially fluid-tight seal with the female connector 1904. The first shaft 1906a may also include at least one channel 1912a disposed between the sealing surface 1910a and a proximal end portion of the first shaft 1906a. Similarly, the second shaft 1906b may include at least one channel 1912b disposed between the sealing surface 1910b and a proximal end portion of the second shaft 1906b. The channel 1912a may extend at least partially circumferentially around the longitudinal axis 206a of the first shaft 1906a, and the channel 1912b may extend at least partially circumferentially around the longitudinal axis 206b of the second shaft 1906b.

As shown in FIG. 19, the bayonet connector 1902 may include an intermediate linkage 1914 separating the first shaft 1906a from the second shaft 1906b. The intermediate linkage 1914 may, for example, be used as a grip or other like support structure when inserting the male bayonet connector 1902 at least partially into the female bayonet connector 1904. The intermediate linkage 1914 may comprise a substantially rigid, substantially planar structure, and the intermediate linkage 1914 may substantially surround the respective outer surfaces of the first and second shafts 1906a, 1906b. The intermediate linkage 1914 may include a distal surface 1916, and a proximal surface 1918 disposed opposite the distal surface 1916. In example embodiments, the distal surface 1916 may be disposed substantially parallel to the proximal surface 1918, and the surfaces 1916, 1918 may extend substantially perpendicular to the longitudinal axes 206a, 206b of the respective shafts 1906a, 1906b. In such embodiments, the intermediate linkage 1914 may have a thickness W extending axially from the distal surface 1916 to the proximal surface 1918. The intermediate linkage 1914 may further include at least one thru hole or other like orifice 1920 extending axially from the distal surface 1916 to the proximal surface 1918. In such examples, the orifice 1920 may extend substantially parallel to the longitudinal axes 206a, 206b. Although illustrated as having a substantially square configuration in FIG. 19, it is understood that the orifice 1920 may have any circular, ovular, triangular, rectangular, elliptical, or other configuration to assist in aligning the male bayonet connector 1902 as at least a portion thereof is inserted into the female connector 1904.

The orifice 1920 may be configured to mate with and/or accept at least a portion of a corresponding structure extending from the female connector 1904 when at least part of the bayonet connector 1902 is inserted into the female connector 1904. For example, the female connector 1904 may include a first orifice 1922a configured to accept passage of at least part of the distal end portion 1908a therethrough, and a second orifice 1922b configured to accept passage of at least part of the distal end portion 1908b therethrough. The female connector 1904 may also include a front face 1924 including at least one extension 1926 extending substantially perpendicularly therefrom. The extension 1926 may be configured to mate with the orifice 1920 when various components of the bayonet connector 1902 form a substantially fluid-tight seal with the female connector 1904. In particular, the extension 1926 may have a shape, size, length, and/or other configuration corresponding to the orifice 1920 such that the extension 1926 may extend at least partially through the orifice 1920 when the bayonet connector 1902 form a substantially fluid-tight seal with the female connector 1904. For example, although the extension 1926 is illustrated as having a substantially square configuration in FIG. 19, in further examples, the extension 1926 may have any circular, ovular, triangular, rectangular, elliptical, or other configuration to assist in aligning the male bayonet connector 1902 as at least a portion thereof is inserted into the female connector 1904. It is understood that in examples in which the bayonet connector 1902 includes one or more additional orifices similar to the orifice 1920, the female connector 1904 may also include one or more corresponding extensions configured to mate with such additional orifices as noted above with respect to the extension 1926.

The example systems and methods of the present disclosure overcome various deficiencies of known prior art devices. Other embodiments of the present disclosure will be apparent to those skilled in the art from consideration of the specification and practice of the disclosure contained herein. It is intended that the specification and examples be considered as example only, with a true scope and spirit of the present disclosure being indicated by the following claims.

What is claimed is:

1. A male bayonet connector, comprising:
a first shaft;
a second shaft extending substantially parallel to the first shaft; and
a link connecting the first shaft with the second shaft, the first shaft including:
  a first distal end portion having a first sealing surface configured to form a substantially fluid-tight seal with a female connector,
  a first proximal end portion opposite the first distal end portion,
  a first lumen extending substantially along a first longitudinal axis of the first shaft from the first distal end portion to the first proximal end portion, and
  a first channel formed on an outer surface of the first shaft between the first sealing surface and the first proximal end portion, the first channel:
    at least partially extending circumferentially around the first longitudinal axis, and
    including a first distal wall, a first proximal wall opposite the first distal wall, a first central region disposed between the first distal wall and the first proximal wall, and a first rib extending radially outwardly from the first central region, wherein:
    the first distal wall extends proximally from a proximal end of the first sealing surface,
    a tapered wall of the first distal end portion extends distally from a distal end of the first sealing surface,
    the first sealing surface comprises a substantially cylindrical surface extending from the proximal end of the first sealing surface to the distal end of the first sealing surface, and
    the first sealing surface is configured to form the first substantially fluid-tight seal at a location between the first distal wall and the tapered wall.

2. The male bayonet connector of claim 1, wherein the first sealing surface is disposed a first radial distance away from the first longitudinal axis, and wherein the first rib includes a radially outermost surface disposed a second radial distance away from the first longitudinal axis substantially equal to the first radial distance, the radially outermost surface extending substantially parallel to the first longitudinal axis.

3. The male bayonet connector of claim 2, wherein the first rib extends from the first proximal wall to the first distal wall.

4. The male bayonet connector of claim 1,
the first distal wall having a substantially convex profile, and extending radially outwardly from the first central region to the proximal end of the first sealing surface.

5. The male bayonet connector of claim 4, the tapered wall having a substantially convex profile, and extending radially inwardly from the distal end of the first sealing surface to a distal end of the first shaft.

6. The male bayonet connector of claim 1, wherein the outer surface of the first shaft comprises a substantially cylindrical outer surface extending from a proximal and radially outwardmost end of the first proximal wall to a barb disposed at the first proximal end portion.

7. The male bayonet connector of claim 1, wherein the second shaft comprises:
  a second distal end portion having a second sealing surface configured to form an additional substantially fluid-tight seal with the female connector,
  a second proximal end portion opposite the second distal end portion,
  a second lumen extending substantially along a second longitudinal axis of the second shaft from the second distal end portion to the second proximal end portion, and
  a second channel formed on an outer surface of the second shaft between the second sealing surface and the second proximal end portion, the second channel
    at least partially extending circumferentially around the second longitudinal axis, and
    including a second distal wall, a second proximal wall opposite the second distal wall, and a second central region extending from the second distal wall to the second proximal wall.

8. The male bayonet connector of claim 7, wherein:
the second sealing surface comprises a substantially cylindrical surface extending distally from the second distal wall,
the second channel includes a second rib extending radially outwardly from the second central region.

9. A male bayonet connector, comprising:
a first shaft;
a second shaft; and
a link connecting the first shaft with the second shaft, the first shaft including:
  a first distal end portion having a first substantially cylindrical sealing surface configured to form a substantially fluid-tight seal with a female connector,
  a first proximal end portion opposite the first distal end portion and including a first barb,
  a first lumen extending substantially along a first longitudinal axis of the first shaft from the first distal end portion to the first proximal end portion,
  a first tapered wall extending distally from a distal end of the first sealing surface, and
  a first channel formed on a first outer surface of the first shaft, the first channel including:
    a first distal wall having a substantially convex profile and extending from a proximal end of the first sealing surface,
    a first proximal wall opposite the first distal wall,
    a first central region disposed between the first distal wall and the first proximal wall, and
    and a first rib extending radially outwardly from the first central region, the first substantially cylindrical sealing surface extending from the proximal end of the first sealing surface to the distal end of the first sealing surface,
  the second shaft including:
    a second lumen extending substantially along a second longitudinal axis of the second shaft, the second longitudinal axis extending substantially parallel to the first longitudinal axis, and
    a second channel formed on a second outer surface of the second shaft, the second channel including a second distal wall having a substantially convex profile, a second proximal wall opposite the second distal wall, and a second central region disposed between the second distal wall and the second proximal wall.

10. The male bayonet connector of claim 9, wherein the first distal wall extends distally and radially outwardly from the first central region to the proximal end of the first sealing surface.

11. The male bayonet connector of claim 10, wherein the first tapered wall extends radially inwardly from the distal end of the first sealing surface.

12. The male bayonet connector of claim 11, wherein
the first tapered wall comprises a substantially convex profile,
a distal end of the first shaft includes a substantially linear profile and extends substantially perpendicular to the first longitudinal axis, and
the first tapered wall terminates at the distal end of the first shaft.

13. The male bayonet connector of claim 12, wherein
the first proximal wall includes a substantially convex profile, and extends proximally and radially outwardly from the first central region to the first outer surface of the first shaft,
the first outer surface extends from a proximal end of the first proximal wall to the first barb, and
the second shaft includes a second barb disposed at a second proximal end portion of the second shaft.

14. The male bayonet connector of claim 9, wherein
the second channel includes a second rib extending radially outwardly from the second central region.

15. A male bayonet connector, comprising:
a first shaft;
a second shaft; and
a link connecting the first shaft with the second shaft, the first shaft including:
a first distal end portion having a first substantially cylindrical sealing surface configured to form a first substantially fluid-tight seal with a female connector,
a first proximal end portion opposite the first distal end portion and including a first barb configured to form a second substantially fluid-tight seal with an inner surface of a tube,
a first lumen extending substantially along a first longitudinal axis of the first shaft from the first distal end portion to the first proximal end portion,
a first channel formed on a first outer surface of the first shaft, the first channel including:
a first distal wall extending from a proximal end of the first sealing surface,
a first proximal wall opposite the first distal wall,
a first central region extending from the first distal wall to the first proximal wall,
a first rib extending radially outwardly from the first central region, and
a first tapered wall extending distally and radially inwardly from a distal end of the first substantially cylindrical sealing surface, the first substantially cylindrical sealing surface extending from the proximal end of the first sealing surface to the distal end of the first sealing surface,
the second shaft including:
a second lumen extending substantially along a second longitudinal axis of the second shaft, the second longitudinal axis extending substantially parallel to the first longitudinal axis,
a second channel formed on a second outer surface of the second shaft, the second channel including a second distal wall, a second proximal wall opposite the second distal wall, and a second central region extending from the second distal wall to the second proximal wall, and
a second proximal end portion opposite the first proximal end portion of the first shaft, the second proximal end portion including a second barb opposite the first barb.

16. The male bayonet connector of claim 15, wherein the second shaft further includes a second distal end portion opposite the second proximal end portion, the second distal end portion having a second substantially cylindrical sealing surface configured to form a third substantially fluid-tight seal with the female connector.

17. The male bayonet connector of claim 15, the first distal wall of the first channel having a first curved profile, and the second distal wall of the second channel having the first curved profile.

18. The male bayonet connector of claim 17, the first proximal wall of the first channel having a second curved profile, and the second proximal wall of the second channel having the second curved profile,
a distal end of the first shaft includes a substantially linear profile and extends substantially perpendicular to the first longitudinal axis, and
the first tapered wall terminates at the distal end of the first shaft.

19. The male bayonet connector of claim 18, wherein at least one of the first curved profile or the second curved profile comprises a substantially convex profile.

20. A male bayonet connector, comprising:
a first shaft;
a second shaft extending substantially parallel to the first shaft; and
a link connecting the first shaft with the second shaft, the first shaft including:
a first distal end portion having a first sealing surface configured to form a substantially fluid-tight seal with a female connector,
a first proximal end portion opposite the first distal end portion,
a first lumen extending substantially along a first longitudinal axis of the first shaft from the first distal end portion to the first proximal end portion, and
a first channel formed on an outer surface of the first shaft between the first sealing surface and the first proximal end portion, the first channel:
at least partially extending circumferentially around the first longitudinal axis, and
including a first distal wall, a first proximal wall opposite the first distal wall, and a first central region disposed between the first distal wall and the first proximal wall, wherein:
the first distal wall extends proximally from a proximal end of the first sealing surface,
a tapered wall of the first distal end portion extends distally from a distal end of the first sealing surface,
the first sealing surface comprises a substantially cylindrical surface extending from the proximal end of the first sealing surface to the distal end of the first sealing surface,
the first sealing surface is configured to form the first substantially fluid-tight seal at a location between the first distal wall and the tapered wall, and the outer surface of the first shaft comprises a substantially cylindrical outer surface extending from a proximal and radially outwardmost end of the first proximal wall to a barb disposed at the first proximal end portion.

* * * * *